US008753795B2

United States Patent
Ichikawa et al.

(10) Patent No.: US 8,753,795 B2
(45) Date of Patent: Jun. 17, 2014

(54) PHOTORESIST COMPOSITION

(75) Inventors: Koji Ichikawa, Osaka (JP); Hiromu Sakamoto, Osaka (JP); Yuichi Mukai, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 7 days.

(21) Appl. No.: 13/428,555

(22) Filed: Mar. 23, 2012

(65) Prior Publication Data

US 2012/0251945 A1 Oct. 4, 2012

(30) Foreign Application Priority Data

Mar. 28, 2011 (JP) ................................ 2011-070035
May 10, 2011 (JP) ................................ 2011-105140

(51) Int. Cl.
*G03F 7/039* (2006.01)
*G03F 7/30* (2006.01)

(52) U.S. Cl.
USPC ..................... 430/280.1; 430/270.1; 430/326

(58) Field of Classification Search
None
See application file for complete search history.

(56) References Cited

U.S. PATENT DOCUMENTS

| | | | | |
|---|---|---|---|---|
| 5,069,998 A * | 12/1991 | Schwalm et al. | ........... | 430/270.1 |
| 6,093,517 A * | 7/2000 | Ito et al. | ................... | 430/270.1 |
| 6,824,954 B2 * | 11/2004 | Yoneda et al. | ............. | 430/270.1 |
| 2004/0063979 A1 * | 4/2004 | Kagawa et al. | ................ | 549/554 |
| 2006/0134558 A1 * | 6/2006 | Kim et al. | ..................... | 430/311 |
| 2007/0100159 A1 | 5/2007 | Yoshida et al. | | |
| 2010/0044654 A1 | 2/2010 | Moy et al. | | |
| 2010/0075983 A1 * | 3/2010 | Gobbi et al. | ............. | 514/254.02 |
| 2010/0080963 A1 * | 4/2010 | Hikita et al. | ............... | 428/195.1 |
| 2010/0122750 A1 | 5/2010 | Erben et al. | | |
| 2010/0324164 A1 | 12/2010 | Higo et al. | | |
| 2011/0070543 A1 * | 3/2011 | Knapp et al. | ............... | 430/280.1 |
| 2011/0200936 A1 | 8/2011 | Ichikawa et al. | | |

FOREIGN PATENT DOCUMENTS

| | | |
|---|---|---|
| DE | 1907117 A * | 6/1977 |
| EP | 0911164 A2 * | 4/1999 |
| EP | 2613198 A1 * | 7/2013 |
| JP | 2010-265408 A * | 11/2010 |
| WO | WO 2009/145167 A1 | 12/2009 |
| WO | WO-2012029758 A * | 3/2012 |

OTHER PUBLICATIONS

Aron Oxetane, OXT-221, OXT technical report, Toagosei Co., Ltd, 5 pages downloaded from http://instantadhesives.aronalpha.net/Asset/TDS%20OXT-221%20.pdf on Oct. 1, 2013.*
Kobayashi et al , SYNLETT, Nov. 1991, pp. 811-813.*
Rousseau et al , Tetrahedron 65 (2009) pp. 8571-8581.*
Miyamoto et al (Journal of Polymer Science; Part A; Polymer Chemistry, vol. 37, pates 445-453 (1999).*
Izquierdo et al Organic Letters,, 2011, vol. 13, No. 15, pp. 3856-3859.*
English translation of JP 2010-265408 A published Nov. 2010 and proffered by applicants on Oct. 17, 2013.*

* cited by examiner

*Primary Examiner* — Cynthia Hamilton
(74) *Attorney, Agent, or Firm* — Birch, Stewart, Kolasch & Birch, LLP

(57) ABSTRACT

The present invention provides a photoresist composition containing: a resin which contains a structural unit derived from a compound having an acid-labile group and which is insoluble or poorly soluble in an alkali aqueous solution but becomes soluble in an alkali aqueous solution by the action of an acid; an acid generator and a compound represented by the formula (I):

$$R^1-X^1-\underset{(R^2)_{u1}}{\underbrace{\phantom{XXXX}}}_{s1}O_{t1} \quad (I)$$

wherein $R^1$, $X^1$, $R^2$, u1, s1, t1 are each defined in the specification, with the proviso that sum of s1 and t1 is 1 or 2.

8 Claims, No Drawings

PHOTORESIST COMPOSITION

This nonprovisional application claims priority under 35 U.S.C. §119(a) on Patent Applications No 2011-070035 filed in JAPAN on Mar. 28, 2011 and No. 2011-105140 filed in JAPAN on May 10, 2011, the entire contents of which are hereby incorporated by reference.

FIELD OF THE INVENTION

The present invention relates to a photoresist composition.

BACKGROUND OF THE INVENTION

A photoresist composition used for semiconductor microfabrication employing a lithography process contains a resin having a structural unit derived from a compound having an acid-labile group, being insoluble or poorly soluble in an alkali aqueous solution but becoming soluble in an alkali aqueous solution by the action of an acid, an acid generator and a basic compound.

US 2007/0122750 A1 discloses a photoresist composition comprising a resin having the structural units represented by the following:

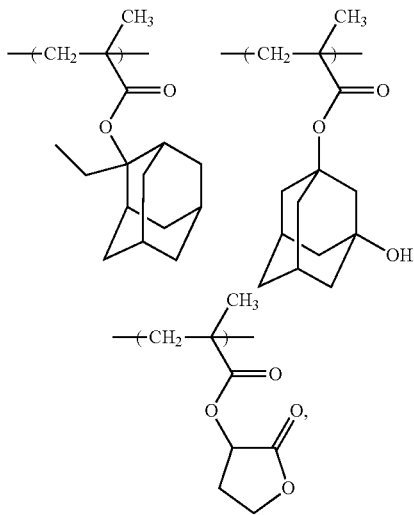

an acid generator represented by the following:

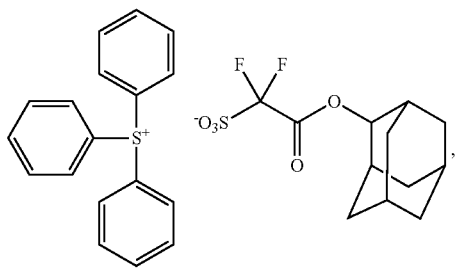

2,6-diisopropylaniline and solvents.

SUMMARY OF THE INVENTION

The present invention is to provide a photoresist composition

The present invention relates to the followings:

<1> A photoresist composition comprising
a resin which comprises a structural unit derived from a compound having an acid-labile group and which is insoluble or poorly soluble in an alkali aqueous solution but becomes soluble in an alkali aqueous solution by the action of an acid,
an acid generator and
a compound represented by the formula (I):

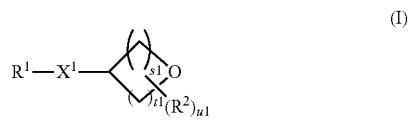

wherein $R^1$ represents a hydroxyl group, a C1-C8 alkyl group, a C3-C12 alicyclic hydrocarbon group or a C6-C18 aromatic hydrocarbon group, and one or more hydrogen atom in the alicyclic hydrocarbon group and the aromatic hydrocarbon group may be substituted with a hydroxyl group or a C1-C6 alkyl group, and one or more —$CH_2$— in the alicyclic hydrocarbon group may be replaced by —O—, —CO—, —S— or —$SO_2$—, $X^1$ represents a C1-C12 divalent saturated hydrocarbon group in which one or more —$CH_2$— may be replaced by —O— or —CO—, $R^2$ is independently in each occurrence a C1-C12 saturated hydrocarbon group, u1 represents an integer of 0 to 2, s1 represents 1 or 2, t1 represents 0 or 1 with the proviso that sum of s1 and t1 is 1 or 2;

<2> The photoresist composition according to <1>, wherein the content of the compound represented by the formula (I) is 0.01 to 5% by mass based on the solid content of the photoresist composition;

<3> The photoresist composition according to <1> or <2>, wherein $X^1$ is *—CO—O—$CH_2$—, *—$CH_2$—O—CO—O—$CH_2$—, *—O—$CH_2$—CO—O—$CH_2$—, or *—O—CO—O—$CH_2$— in which * represents a binding position to $R^1$;

<4> The photoresist composition according to <1> or <2>, wherein $X^1$ is *—CO—O—$CH_2$— in which * represents a binding position to $R^1$;

<5> The photoresist composition according to any one of <1> to <4>, wherein $R^1$ is a C6-C12 alicyclic hydrocarbon group or a C6-C12 aromatic hydrocarbon group, and one or more hydrogen atom in the alicyclic hydrocarbon group and the aromatic hydrocarbon group may be substituted with a hydroxyl group or a C1-C6 alkyl group, and one or more —$CH_2$— in the alicyclic hydrocarbon group may be replaced by —O— or —$SO_2$—;

<6> The photoresist composition according to any one of <1> to <4>, wherein $R^1$ is a C6-C12 alicyclic hydrocarbon group in which one or more hydrogen atom may be substituted with a hydroxyl group or a C1-C6 alkyl group, and in which one or more —$CH_2$— may be replaced by —O— or —$SO_2$—;

<7> The photoresist composition according to any one of <1> to <6>, wherein $R^2$ is independently in each occurrence a C1-C12 alkyl group;

<8> A process for producing a photoresist pattern comprising the following steps (1) to (5);
(1) a step of applying the photoresist composition according to any one of <1> to <7> on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern;

<9> A compound represented by the formula (I');

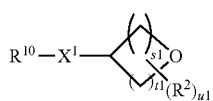
(I')

wherein $R^{10}$ represents a C1-C8 alkyl group or a C3-C12 alicyclic hydrocarbon group, and one or more hydrogen atom in the alicyclic hydrocarbon group may be substituted with a hydroxyl group or a C1-C6 alkyl group, and one or more —$CH_2$— in the alicyclic hydrocarbon group may be replaced by —O—, —CO—, —S— or —$SO_2$—, $X^1$ represents a C1-C12 divalent saturated hydrocarbon group in which one or more —$CH_2$— may be replaced by —O— or —CO—, $R^2$ is independently in each occurrence a C1-C12 saturated hydrocarbon group, u1 represents an integer of 0 to 2, s1 represents 1 or 2, t1 represents 0 or 1 with the proviso that sum of s1 and t1 is 1 or 2;

<10> The compound according to <9>, wherein $X^1$ is *—CO—O—$CH_2$—, *—$CH_2$—O—CO—O—$CH_2$—, *—O—$CH_2$—CO—O—$CH_2$—, or *—O—CO—O—$CH_2$— in which * represents a binding position to $R^{10}$;

<11> The compound according to <9>, wherein $X^1$ is *—CO—O—$CH_2$— in which * represents a binding position to $R^{10}$;

<12> The compound according to any one of <9> to <11>, wherein $R^{10}$ is a C6-C12 alicyclic hydrocarbon group in which one or more hydrogen atom may be substituted with a hydroxyl group or a C1-C6 alkyl group, and in which one or more —$CH_2$— may be replaced by —O— or —$SO_2$—;

<13> The compound according to any one of <9> to <12>, wherein $R^2$ is independently in each occurrence a C1-C12 alkyl group.

DESCRIPTION OF PREFERRED EMBODIMENTS

The photoresist composition of the present invention comprises a resin which comprises a structural unit derived from a compound having an acid-labile group and which is insoluble or poorly soluble in an alkali aqueous solution but becomes soluble in an alkali aqueous solution by the action of an acid,
an acid generator and
a compound represented by the formula (I):

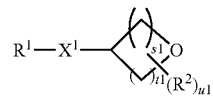
(I)

(hereinafter, simply referred to as the compound (I)).

In the formula (I), $R^1$ represents a hydroxyl group, a C1-C8 alkyl group, a C3-C12 alicyclic hydrocarbon group or a C6-C18 aromatic hydrocarbon group, and one or more hydrogen atom in the alicyclic hydrocarbon group and the aromatic hydrocarbon group may be substituted with a hydroxyl group or a C1-C6 alkyl group, and one or more —$CH_2$— in the alicyclic hydrocarbon group may be replaced by —O—, —CO—, —S— or —$SO_2$—, $X^1$ represents a C1-C12 divalent saturated hydrocarbon group in which one or more —$CH_2$— may be replaced by —O— or —CO—, $R^2$ is independently in each occurrence a C1-C12 saturated hydrocarbon group, u1 represents an integer of 0 to 2, s1 represents 1 or 2, t1 represents 0 or 1 with the proviso that sum of s1 and t1 is 1 or 2.

First, the compound (X) will be illustrated.

Examples of the C1-C8 alkyl group represented by $R^1$ include a C1-C8 linear alkyl group such as a methyl group, an ethyl group, a propyl group, a butyl group, a pentyl group and a hexyl group, and a C3-C8 branched chain alkyl group such as an isopropyl group, a 1-methyl-1-propyl group, a 2-methyl-1-propyl group, a 1-methyl-1-butyl group, a 2-methyl-1-butyl group and a 2-ethyl-hexyl group.

The alicyclic hydrocarbon group represented by $R^1$ may be monocyclic or polycyclic. Examples of the C3-C12 alicyclic hydrocarbon group represented by $R^1$ include a cyclopropyl group, a cylobutyl group, a cyclopentyl group, a cyclohexyl group, a 1-adamantyl group, and the following group:

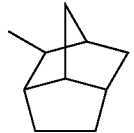

Examples of the C6-C18 aromatic hydrocarbon group represented by $R^1$ include a phenyl group and a naphthyl group.

One or more hydrogen atom in the above-mentioned alicyclic hydrocarbon group and the above-mentioned aromatic hydrocarbon group may be substituted with a hydroxyl group or a C1-C6 alkyl group such as a methyl group, an ethyl group, a propyl group, an isopropyl group, a butyl group, an isobutyl group, a tert-butyl group, a pentyl group, a hexyl group.

One or more —$CH_2$— in the alicyclic hydrocarbon group may be replaced by —O—, —CO—, —S— or —$SO_2$—, and examples of the alicyclic hydrocarbon group in which one or more —$CH_2$— are replaced by —O—, —CO—, —S— or —$SO_2$— include the following groups.

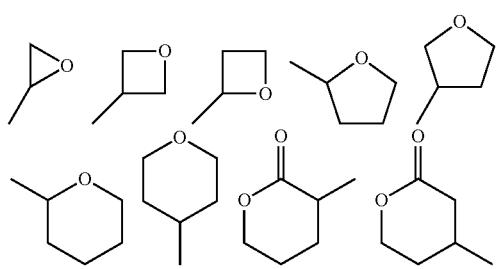

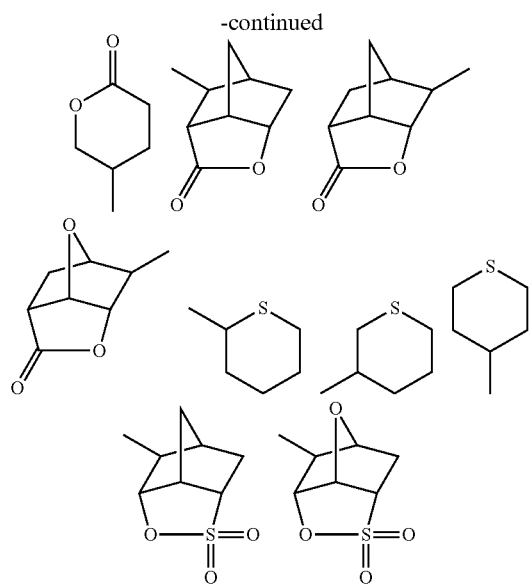

R¹ is preferably a C3-C12 alicyclic hydrocarbon group in which one or more hydrogen atom may be substituted with a hydroxyl group or a C1-C6 alkyl group, and in which one or more —CH$_2$— may be replaced by —O—, —CO—, —S— or —SO$_2$—, or a C6-C18 aromatic hydrocarbon group in which one or more hydrogen atom may be substituted with a hydroxyl group or a C1-C6 alkyl group. R¹ is more preferably a C3-C12 alicyclic hydrocarbon group in which one or more hydrogen atom may be substituted with a hydroxyl group or a C1-C6 alkyl group, and in which one or more —CH$_2$— may be replaced by —O—, —CO—, —S— or —SO$_2$—.

Examples of the C1-C12 divalent saturated hydrocarbon group represented by X¹ include a C1-C12 linear alkanediyl group such as a methylene group, an ethylene group, a propane-1,3-diyl group, a propane-1,2-diyl group, a butane-1,4-diyl group, a pentane-1,5-diyl group, a hexane-1,6-diyl group, a heptane-1,7-diyl group and an octane-1,8-diyl group; a C4-C12 branched chain alkanediyl group such as a butane-1,3-diyl group, a 2-methylopropane-1,3-diyl group, a 2-methylpropane-1,2-diyl group, a pentane-1,4-diyl group and a 2-methylbutane-1,4-diyl group; a C3-C12 divalent alicyclic hydrocarbon group such as a cyclobutane-1,3-diyl group, a cyclopentane-1,3-diyl group, a cyclohexane-1,4-diyl group and a cyclooctane-1,5-diyl group; and a group formed by combining two or more groups selected from the group consisting of the above-mentioned C1-C12 linear alkanediyl group, the above-mentioned C4-C12 branched chain alkanediyl group and the above-mentioned C3-C12 divalent alicyclic hydrocarbon group.

One or more —CH$_2$— in the C1-C12 divalent saturated hydrocarbon group may be replaced by —O— or —CO—, and examples of the C1-C12 divalent saturated hydrocarbon group in which one or more —CH$_2$— are replaced by —O— or —CO— include *—O—CH$_2$—, *—CO—O—CH$_2$—, *—CH$_2$—O—CO—O—CH$_2$—, *—O—CH$_2$—CO—O—CH$_2$—, or *—O—CO—O—CH$_2$— in which * represents a binding position to R¹, and *—CO—O—CH$_2$—, *—CH$_2$—O—CO—O—CH$_2$—, *—O—CH$_2$—CO—O—CH$_2$—, and *—O—CO—O—CH$_2$— are preferable, and *—CO—O—CH$_2$— is more preferable.

In the formula (I), s1 is preferably 1, t1 is preferably 1, and sum of s1 and t1 is preferably 2.

Examples of the C1-C12 saturated hydrocarbon group represented by R² include a C1-C12 alkyl group, a C3-C12 saturated alicyclic hydrocarbon group, and a group formed by combining a C1-C12 alkyl group and a C3-C12 saturated alicyclic hydrocarbon group, Examples of the C1-C12 alkyl group include a methyl group, an ethyl group, a propyl group, a butyl group, a pentyl group, a hexyl group, an octyl group, a nonyl group, a decyl group, a dodecyl group, an isopropyl group, an isobutyl group, a tert-butyl group, a 1-methyl-1-propyl group, a 2-methyl-1-propyl group, a 1-methyl-1-butyl group, a 2-methyl-1-butyl group and a 2-ethyl-hexyl group. The saturated alicyclic hydrocarbon group may be monocyclic or polycyclic. Examples of the monocyclic saturated alicyclic hydrocarbon group include a cycloalkyl group such as a cyclopentyl group, a cyclohexyl group, a methylcyclohexyl group, a dimethylcyclohexyl group, a cycloheptyl group and a cyclooctyl group. Examples of the polycyclic saturated alicyclic hydrocarbon group include a decahydronaphthyl group, an adamantyl group, a norbornyl group, a methylnorbornyl group, and the followings:

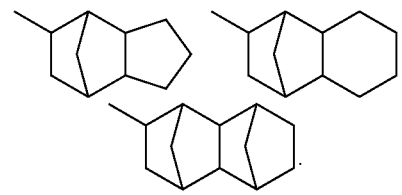

R² is preferably a C1-C12 alkyl group and more preferably a C1-C6 alkyl group.

The compound (I) is preferably one of the following compounds.

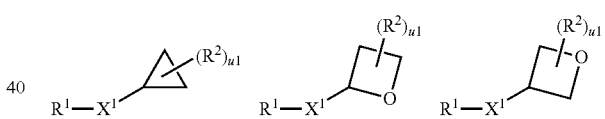

wherein R¹, X¹, R² and u1 are the same as described above.

Specific examples of the compound (I) include the following.

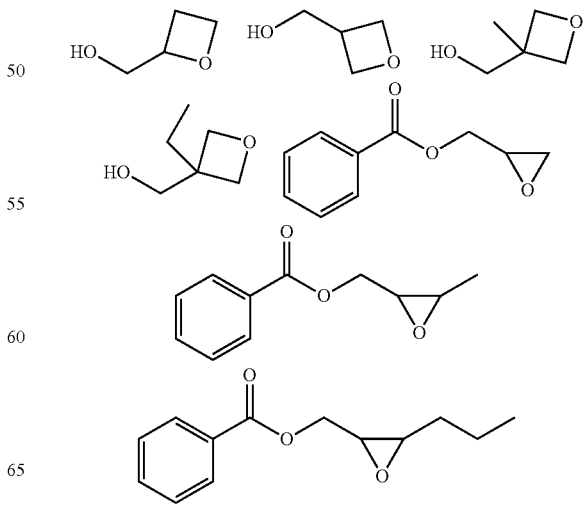

-continued
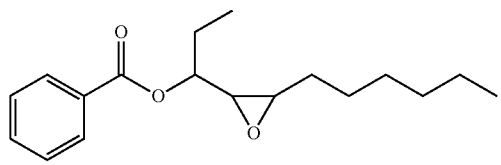
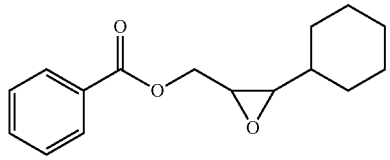
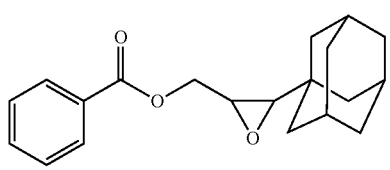
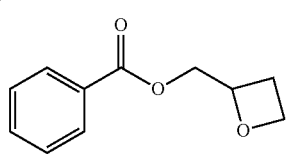
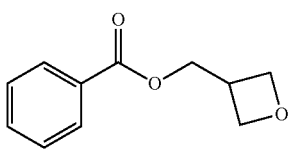
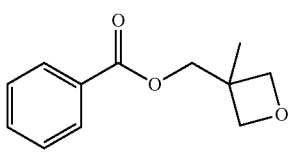
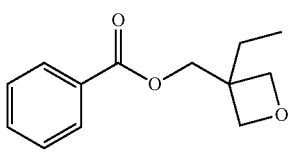
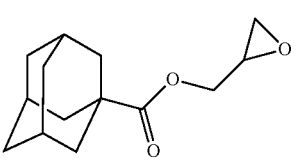
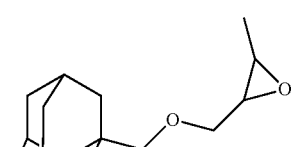
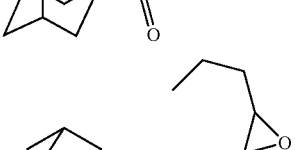
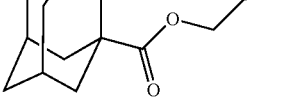
-continued
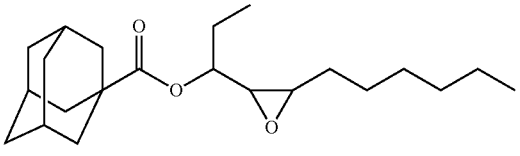
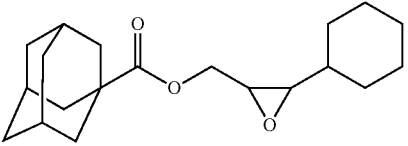
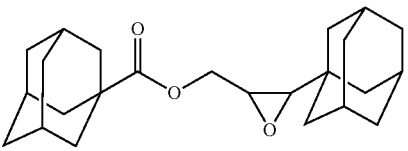
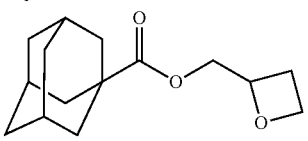
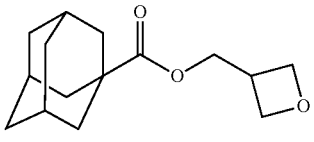
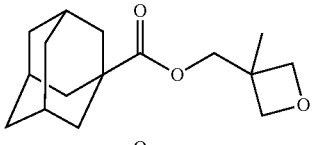
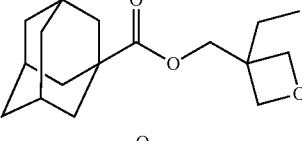
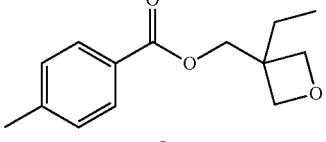
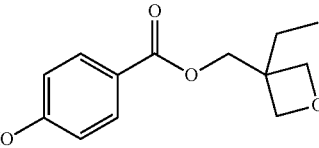
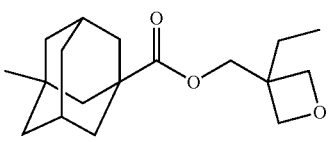
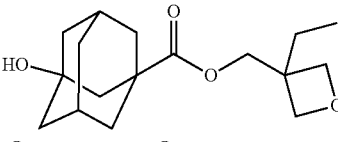
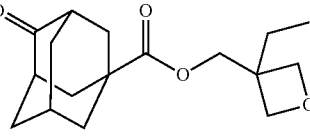

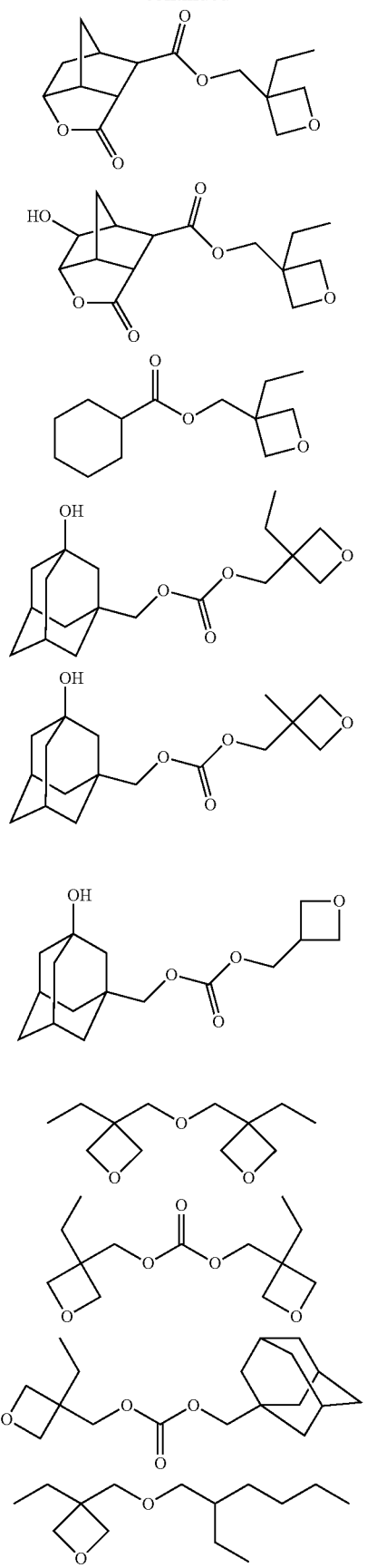

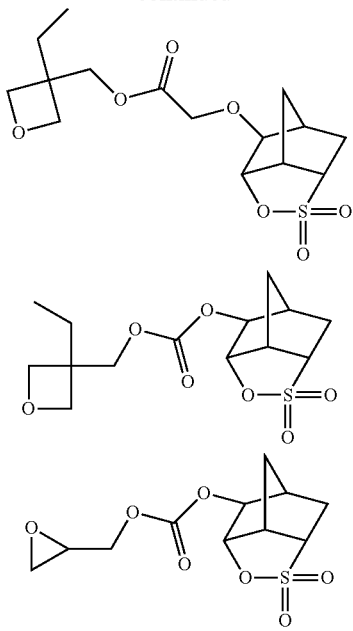

The compound (I) wherein $X^1$ is *—CO—O—CH$_2$— can be produced, for example, by reacting a compound represented by the formula (IA-1) with a compound represented by the formula (IA-2) in the presence of a basic catalyst such as pyridine in a solvent such as chloroform.

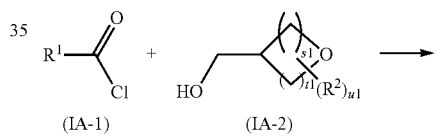

wherein $R^1$, $R^2$, s1, t1 and u1 are the same as defined above.

Examples of the compound represented by the formula (IA-1) include the following.

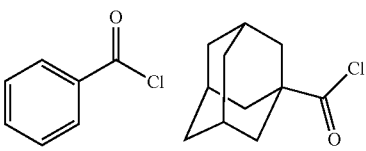

Examples of the compound represented by the formula (IA-2) include the following, and a commercially available one may be used, or one produced according to the known process may be used.

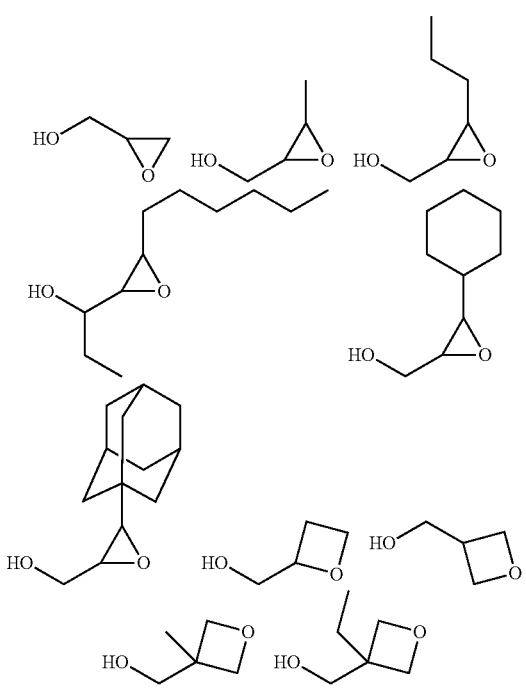

The compound (I) wherein $X^1$ is *—$CH_2$—O—CO—O—$CH_2$— can be produced, for example, by reacting a compound represented by the formula (IA-3) with a compound represented by the formula (IA-2).

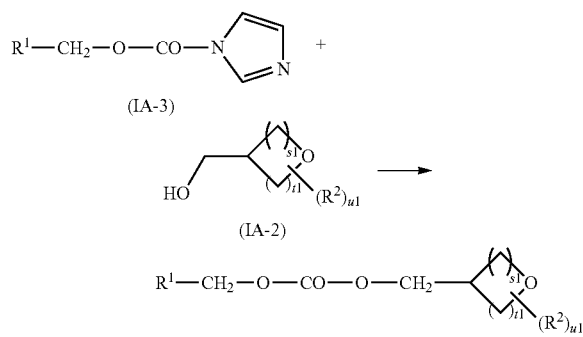

The compound represented by the formula (IA-3) can be produced by reacting a compound represented by the formula (IA-4) with carbonyldiimidazole.

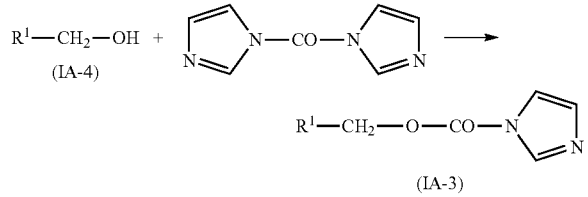

The content of the compound (I) in the photoresist composition of the present invention is usually 0.01% by mass to 5% by mass based on sum of solid component, and preferably 0.1% by mass to 4% by mass. In this specification, "solid component" means components other than solvent in the photoresist composition.

The compound (I) wherein $R^1$ is a C1-C8 alkyl group or a C3-C12 alicyclic hydrocarbon group, and one or more hydrogen atom in the alicyclic hydrocarbon group may be substituted with a hydroxyl group or a C1-C6 alkyl group, and one or more —$CH_2$— in the alicyclic hydrocarbon group may be replaced by —O—, —CO—, —S— or —$SO_2$—, that is, the compound represented by the formula (I'):

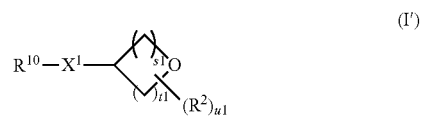

(I')

wherein $R^{10}$ represents a C1-C8 alkyl group, a C3-C12 alicyclic hydrocarbon group, and one or more hydrogen atom in the alicyclic hydrocarbon group may be substituted with a hydroxyl group or a C1-C6 alkyl group, and one or more —$CH_2$— in the alicyclic hydrocarbon group may be replaced by —O—, —CO—, —S— or —$SO_2$—, and $X^1$, $R^2$, u1, s1 and t1 are the same as defined above, is a novel compound.

In the formula (I'), $X^1$ is preferably *—CO—O—$CH_2$—, *—$CH_2$—O—CO—O—$CH_2$—, *—O—$CH_2$—CO—O—$CH_2$—, or *—O—CO—O—$CH_2$— in which * represents a binding position to $R^{10}$, and more preferably *—CO—O—$CH_2$— in which * represents a binding position to $R^{10}$.

In the formula (I'), $R^{10}$ is preferably a C6-C12 alicyclic hydrocarbon group in which one or more hydrogen atom maybe substituted with a hydroxyl group or a C1-C6 alkyl group and in which one or more —$CH_2$— may be replaced by —O— or —$SO_2$—, In the formula (I'), it is preferred that $R^2$ is independently in each occurrence a C1-C12 alkyl group.

Next, the resin will be illustrated.

The resin is insoluble or poorly soluble in an alkali aqueous solution but becomes soluble in an alkali aqueous solution by the action of an acid. The resin has a structural unit derived from a compound having an acid-labile group, and can be produced by polymerizing one or more compounds having an acid-labile group.

In this specification, "an acid-labile group" means a group capable of being eliminated by the action of an acid.

Examples of the acid-labile group include a group represented by the formula (10):

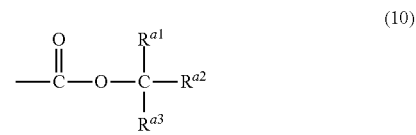

(10)

wherein $R^{a1}$, $R^{a2}$ and $R^{a3}$ independently each represent a C1-C8 alkyl group or a C3-C20 alicyclic hydrocarbon group, and $R^{a1}$ and $R^{a2}$ can be bonded each other to form a C2-C20 divalent hydrocarbon group which forms a ring together with the carbon atom to which they are bonded, and one or more —$CH_2$— in the C1-C8 alkyl group, the C3-C20 alicyclic hydrocarbon group and the C3-C20 divalent hydrocarbon group can be replaced by —O—, —S— or —CO—.

Examples of the C1-C8 alkyl group include a methyl group, an ethyl group, a propyl group, an isopropyl group, a butyl group, a pentyl group, a hexyl group, a heptyl group and an octyl group. The alicyclic hydrocarbon group may be monocyclic or polycyclic, and may be saturated or non-aromatic unsaturated. Examples thereof include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

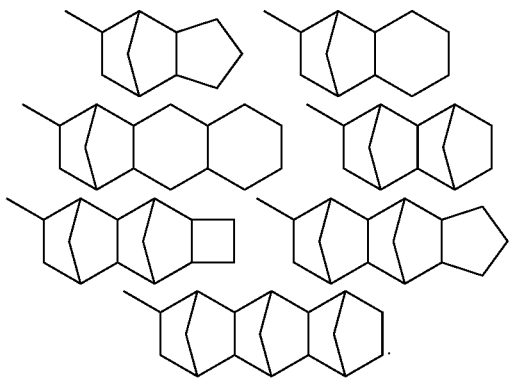

The alicyclic hydrocarbon group is preferably a saturated cyclic hydrocarbon group, and preferably has 3 to 16 carbon atoms.

Examples of the ring formed by bonding $R^{a1}$ and $R^{a2}$ each other include the following groups and the ring preferably has 3 to 12 carbon atoms.

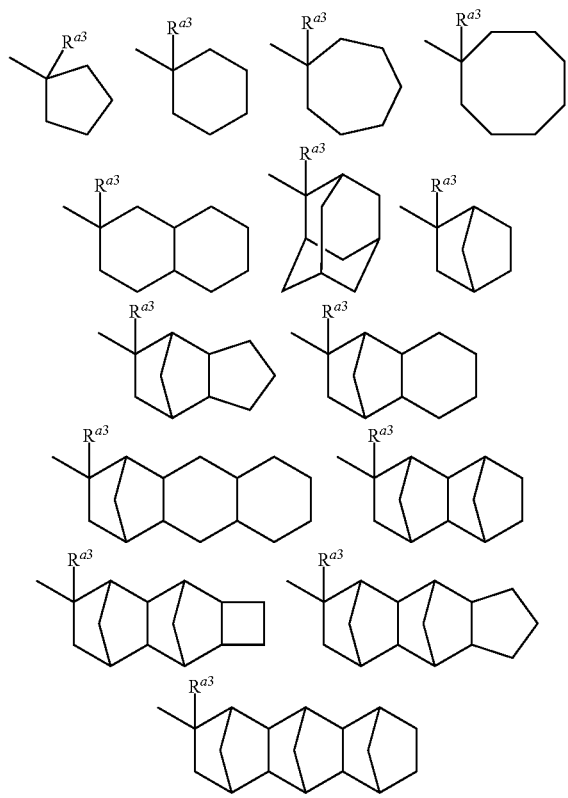

wherein $R^{a3}$ is the same as defined above.

The group represented by the formula (10) wherein $R^{a1}$, $R^{a2}$ and $R^{a3}$ independently each represent a C1-C8 alkyl group such as a tert-butyl group, the group represented by the formula (10) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (10) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

Examples of the acid-labile group include a group represented by the formula (20):

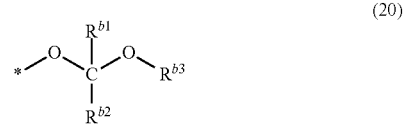

(20)

wherein $R^{b1}$ and $R^{b2}$ independently each represent a hydrogen atom or a C1-C12 hydrocarbon group, and $R^{b3}$ represents a C1-C20 hydrocarbon group, and $R^{b2}$ and $R^{b3}$ can be bonded each other to form a C2-C20 divalent hydrocarbon group which forms a ring together with the carbon atom and the oxygen atom to which they are bonded, and one or more —$CH_2$— in the hydrocarbon group and the divalent hydrocarbon group can be replaced by —O—, —S— or —CO—.

The group represented by the formula (20) has an acetal structure.

Examples of the hydrocarbon group include an aliphatic hydrocarbon group, an alicyclic hydrocarbon group and an aromatic hydrocarbon group. Examples of the aromatic hydrocarbon group include an aryl group such as a phenyl group, a naphthyl group, an anthryl group, a p-methylphenyl group, a p-tert-butylphenyl group, a p-adamantylphenyl group, a tolyl group, a xylyl group, a cumyl group, a mesityl group, a biphenyl group, a phenathryl group, a 2,6-diethylphenyl group and a 2-methyl-6-ethylphenyl group.

It is preferred that at least one of $R^{b1}$ and $R^{b2}$ is a hydrogen atom.

Examples of the group represented by the formula (20) include the following.

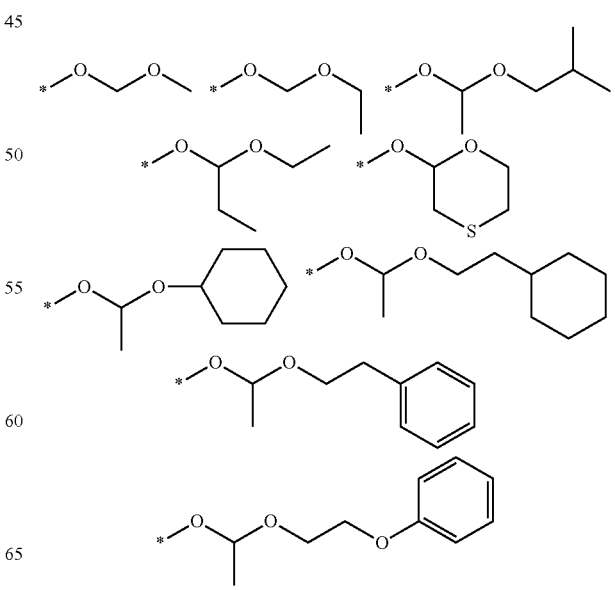

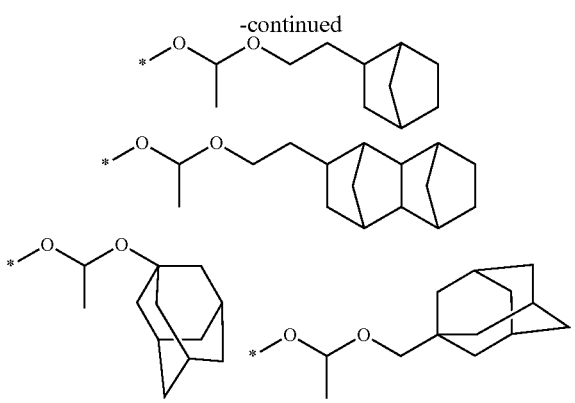

The compound having an acid-labile group is preferably a monomer having an acid-labile group in its side chain and a carbon-carbon double bond, and is more preferably an acrylate monomer having an acid-labile group in its side chain or a methacryalte monomer having an acid-labile group in its side chain.

A monomer having the group represented by the formula (10) or (20) in its side chain and a carbon-carbon double bond is preferable, and an acrylate monomer having the group represented by the formula (10) in its side chain or a methacryalte monomer having the group represented by the formula (10) in its side chain is more preferable.

An acrylate monomer having the group represented by the formula (10) in which $R^{a1}$ and $R^{a2}$ are bonded each other to form a C5-C20 alicycle together with the carbon atom to which they are bonded in its side chain or a methacryalte monomer having the group represented by the formula (10) in which $R^{a1}$ and $R^{a2}$ are bonded each other to form a C5-C20 alicycle together with the carbon atom to which they are bonded in its side chain is especially preferable.

Preferable examples of the compound having an acid-labile group include monomers represented by the formulae (a1-1) and (a1-2):

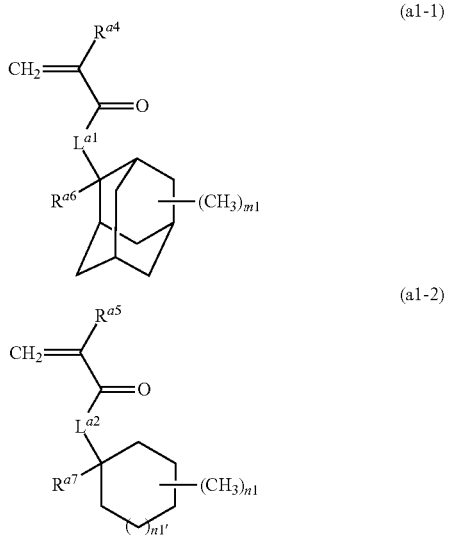

wherein $R^{a4}$ and $R^{a5}$ each independently represents a hydrogen atom Or a methyl, group, $R^{a6}$ and $R^{a7}$ each independently represents a C1-C8 aliphatic hydrocarbon group or a C3-C10 alicyclic hydrocarbon group, $L^{a1}$ and $L^{a2}$ each independently represents *—O— or *—O—$(CH_2)_{k1}$—CO—O— in which * represents a binding position to —CO—, and k1 represents an integer of 1 to 7, and m1 represents an integer of 0 to 14, n1 represents an integer of 0 to 10, and n1' represents an integer of 0 to 3.

The aliphatic hydrocarbon group preferably has 1 to 6 carbon atoms, and the alicyclic hydrocarbon group preferably has 3 to 8 carbon atoms and more preferably 3 to 6 carbon atoms. The alicyclic hydrocarbon group is preferably a saturated aliphatic cyclic hydrocarbon group.

Examples of the aliphatic hydrocarbon group include a C1-C8 alkyl group such as a methyl group, an ethyl group, a propyl group, an isopropyl group, a butyl group, a tert-butyl group, a 2,2-dimethylethyl group, a 1-nethylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl, group, a 1,4-dimethylhexyl group, a heptyl group, a 1-methylheptyl group and an octyl group. Examples of the saturated cyclic hydrocarbon group include a cyclohexyl group, a methylcyclohexyl group, a dimethylcyclohexyl group, a cycloheptyl group, a methylcycloheptyl group, a norbornyl group, a methylnorbornyl group and the following groups.

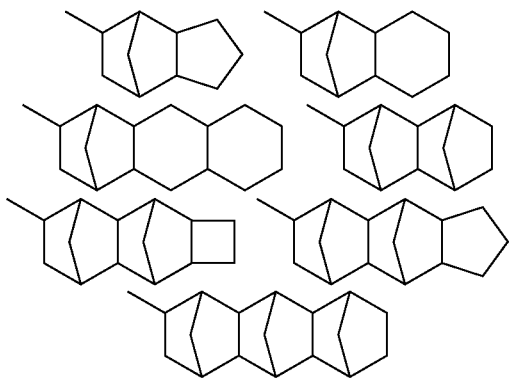

$L^{a1}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—. $L^{a2}$ is preferably *—O— or *—O—$(CH_2)_{f1}$—CO—O— in which * represents a binding position to —CO—, and f1 is the same as defined above, and is more preferably *—O— or *—O—$CH_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1, and n1' is preferably 0 or 1.

$R^{a4}$ and $R^{a5}$ are preferably methyl groups.

Particularly when the photoresist composition contains a resin derived from a monomer having a bulky structure such as a saturated cyclic hydrocarbon group, the photoresist composition having excellent resolution tends to be obtained.

Examples of the monomer represented by the formula (a1-1) include the monomers described in JP 2010-204646 A. Among them, preferred are the monomers represented by the formulae (a1-1-1) to (a1-1-B), and more preferred are the monomers represented by the formulae (a1-1-1) to (a1-1-4).

(a1-1-1) 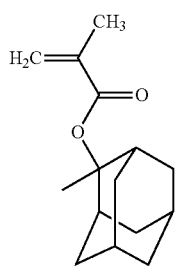

(a1-1-2) 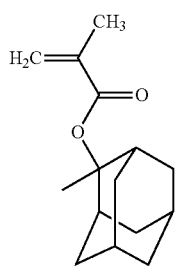

(a1-1-3) 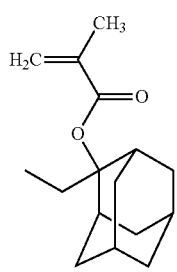

(a1-1-4) 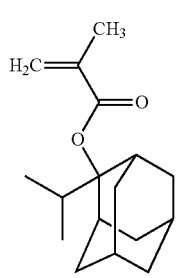

(a1-1-5) 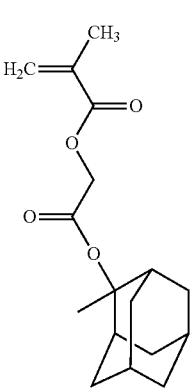

(a1-1-6) 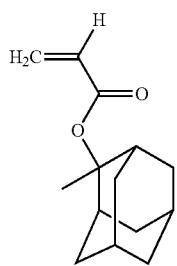

(a1-1-7)

(a1-1-8)

Examples of the monomer represented by the formula (a1-2) include 1-ethylcyclopentan-1-yl acrylate, 1-ethylcyclopentan-1-yl methacrylate, 1-ethylcyclohexan-1-yl acrylate, 1-ethylcyclohexan-1-yl methacrylate, 1-ethylcycloheptan-1-yl acrylate, 1-ethylcycloheptan-1-yl methacrylate, 1-methylcyclopentan-1-yl acrylate, 1-methylcyclopentan-1-yl methacrylate, 1-isopropylcyclopentan-1-yl acrylate and 1-isopropylcyclopentan-1-yl methacrylate. Among them, preferred are the monomers represented by the formulae (a1-2-1) to (a1-2-6), and more preferred are the monomers represented by the formulae (a1-2-3) and (a1-2-4), and still more preferred is the monomer represented by the formula (a1-2-3).

(a1-2-1) 

(a1-2-2)
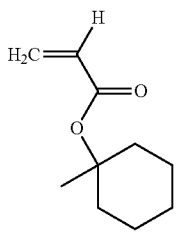

(a1-2-3)
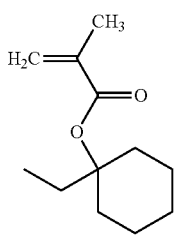

(a1-2-4)
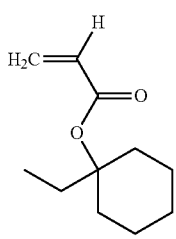

(a1-2-5)
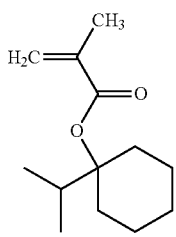

(a1-2-6)
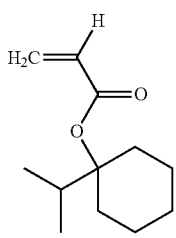

The content of the structural unit derived from a compound having an acid-labile group in the resin is usually 10 to 95% by mole, preferably 15 to 90% by mole and more preferably 20 to 85% by mole based on 100% by mole of all the structural units of the resin.

When the resin contains the structural unit derived from the monomer represented by the formula (a1-1) or (a1-2), the content of the structural unit derived from the monomer represented by the formula (a1-1) or (a1-2) in the resin is usually 10 to 95% by mole, preferably 15 to 90% by mole and more preferably 20 to 85% by mole based on 100% by mole of all the structural units of the resin.

Other examples of the compound having an acid-labile group include a monomer represented by the formula (a1-5):

(a1-5)
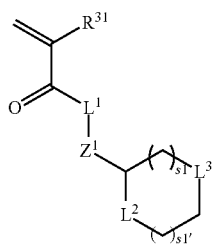

wherein $R^{31}$ represents a hydrogen atom, a halogen atom, a C1-C6 alkyl group which may be substituted with a halogen atom, $L^1$ represents —O—, —S— or *—O—$(CH_2)_{k1}$—CO—O—, k1 represents an integer of 1 to 7, * represents a binding position to —CO—, $L^2$ and $L^3$ independently each represent —O— or —S—, $Z^1$ represents a single bond or a C1-C6 alkylene group in which one or more —$CH_2$— may be replaced by —O— or —CO—, s1 and s1' independently each represent an integer of 0 to 4.

Examples of the halogen atom include a fluorine atom, a chlorine atom and a bromine atom.

Examples of the C1-C6 alkyl group which may be substituted with a halogen atom include a methyl group, an ethyl group, a propyl group, an isopropyl group, a butyl group, an isobutyl group, a sec-butyl group, a text-butyl group, a pentyl group, a hexyl group, a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a perchioromethyl group, a perbromomethyl group and a periodomethyl group, and a C1-C4 alkyl group is preferable and a C1-C2 alkyl group is more preferable and a methyl group is especially preferable.

$R^{31}$ is preferably a hydrogen atom or a methyl group.

$L^1$ is preferably —O—.

It is preferred that one of $L^2$ and $L^3$ is —O— and the other is —S—,

In the formula (a1-5), s1 is preferably 1 and s1' is preferably 0, 1 or 2.

$Z^1$ is preferably a single bond, *—$(CH_2)_{n4}$—O— or *—$(CH_2)_{n4}$—CO—O— in which n4 represents an integer of 1 to 4, and * represents a binding position to $L^4$, and more preferably a single bond, —$CH_2$—O— or —$CH_2$—CO—O—.

Examples of the monomer represented by the formula (a1-5) include the following.

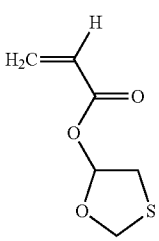 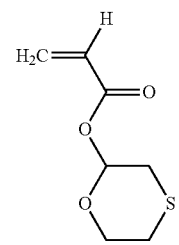 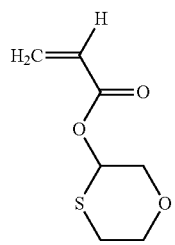

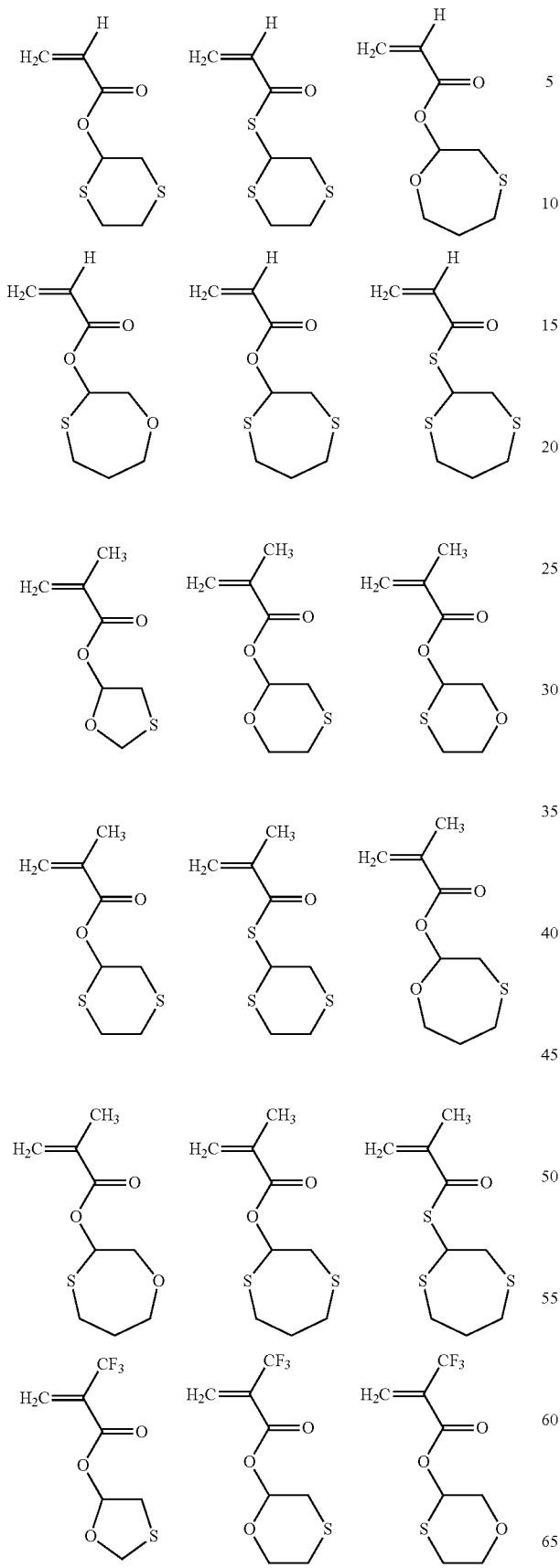
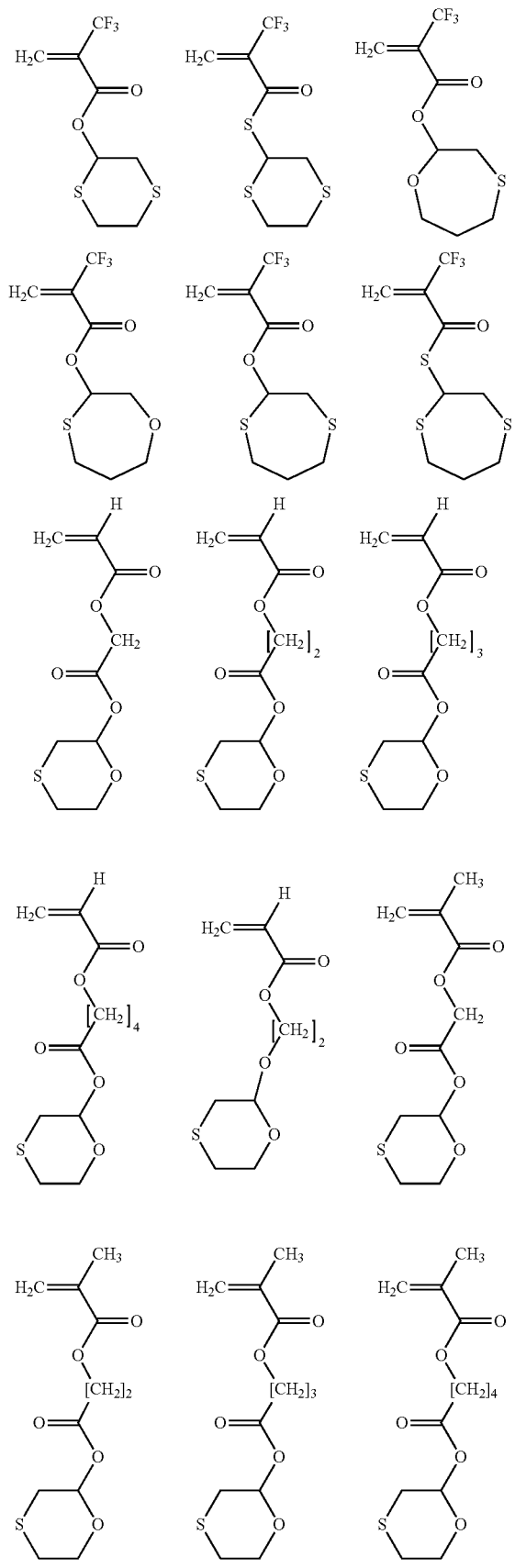

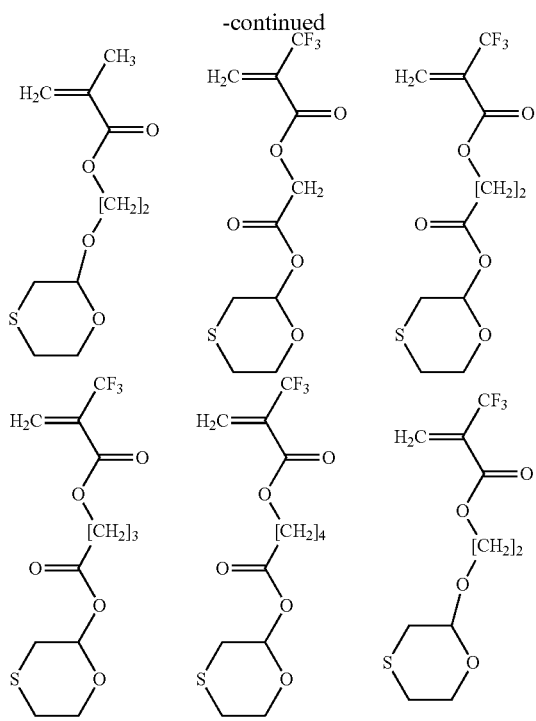

When the resin contains the structural unit derived form the monomer represented by the formula (a1-5), the content of the structural unit derived from the monomer represented by the formula (a1-5) is usually 1 to 95% by mole and preferably 3 to 90% by mole and more preferably 5 to 85% by mole based on total molar of all the structural units of the resin.

The resin can have two or more kinds of structural units derived from the compounds having an acid-labile group.

The resin preferably contains the structural unit derived from the compound having an acid-labile group and a structural unit derived from the compound having no acid-labile group. The resin can have two or more kinds of structural units derived from the compounds having no acid-labile group. When the resin contains the structural unit derived from the compound having an acid-labile group and the structural unit derived from the compound having no acid-labile group, the content of the structural unit derived from the compound having an acid-labile group is usually 10 to 80% by mole and preferably 20 to 60% by mole based on total molar of all the structural units of the resin. The content of the structural unit derived from a monomer having an adamantyl group, especially the monomer represented by the formula (a1-1) in the structural unit derived from the compound having no acid-labile group is preferably 15% by mole or more from the viewpoint of dry-etching resistance of the photoresist composition.

The compound having no acid-labile group preferably contains one or more hydroxyl groups or a lactone ring. When the resin contains the structural unit derived from the compound having no acid-labile group and having one or more hydroxyl groups or a lactone ring, a photoresist composition having good resolution and adhesiveness of photoresist to a substrate tends to be obtained.

Examples of the compound having no acid-labile group and having one or more hydroxyl groups include a monomer represented by the formula (a2-0):

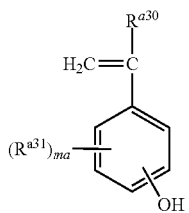

wherein $R^{a30}$ represents a hydrogen atom, a halogen atom or a C1-C6 alkyl group which may have one or more halogen atoms, $R^{a31}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and a monomer represented by the formula (a2-1):

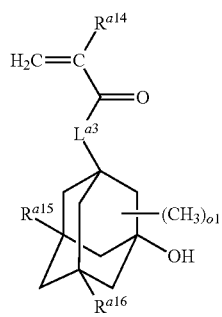

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and of represents an integer of 0 to 10.

When KrF excimer laser (wavelength; 248 nm) lithography system, or a high energy laser such as electron beam (EB) and extreme ultraviolet (EUV) is used as an exposure system, the resin containing the structural unit derived from the monomer represented by the formula (a2-0) is preferable, and when ArF excimer laser (wavelength: 193 nm) is used as an exposure system, the resin containing the structural unit derived from the monomer represented by the formula (a2-1) is preferable.

In the formula (a2-0), examples of the halogen atom include a fluorine atom, examples of the C1-C6 alkyl, group which may have one or more halogen atoms include a methyl group, an ethyl group, a propyl group, an isopropyl group, a butyl group, an isobutyl group, a sec-butyl group, a tert-butyl group, a pentyl group, a hexyl group, a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group, and a C1-C4 alkyl group is preferable and a C1-C2 alkyl group is more preferable and a methyl group is especially preferable. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit derived from the monomer represented by the formula (a2-0) can be produced, for example, by polymerizing a monomer obtained by protecting a hydroxyl group of the monomer represented by the formula (a2-0) with a protecting group such as an acetyl group followed by conducting deprotection of the obtained polymer with a base.

Examples of the monomer represented by the formula (a2-0) include the monomers described in JP 2010-204634 A, and the monomers represented by the formulae (a2-0-1) and (a2-0-2).

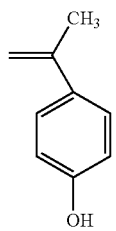

(a2-0-1)

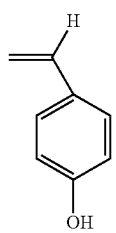

(a2-0-2)

When the resin containing the structural unit derived from the monomer represented by the formula (a2-0) is produced, a monomer of which hydroxyl group is protected with a suitable protecting group can be used.

When the resin contains the structural unit derived from the monomer represented by the formula (a2-0), the content of the structural unit derived from the monomer represented by the formula (a2-0) is usually 5 to 90% by mole and preferably 10 to 85% by mole and more preferably 15 to 80% by mole based on total molar of all the structural units of the resin.

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—(CH$_2$)$_{f2}$—CO—O— in which * represents a binding position to —CO—, and f2 represents an integer of 1 to 4, and is more preferably *—O—, and o1 is preferably 0, 1, 2 or 3 and is more preferably 0 or 1.

Examples of the monomer represented by the formula (a2-1) include the monomers described in JP 2010-204646 A, and the monomers represented by the formulae (a2-1-1) to (a2-1-6) are preferable, and the monomers represented by the formulae (a2-1-1) to (a2-1-4) are more preferable, and the monomers represented by the formulae (a2-1-1) and (a2-1-3).

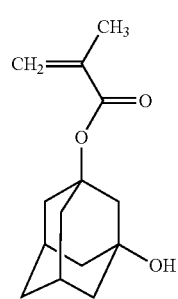

(a2-1-1)

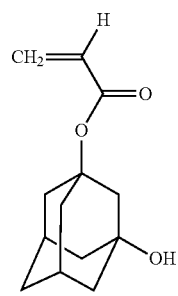

(a2-1-2)

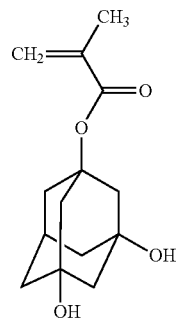

(a2-1-3)

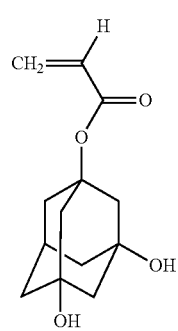

(a2-1-4)

(a2-1-5)

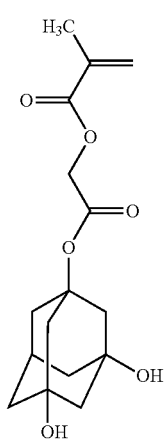

(a2-1-6)

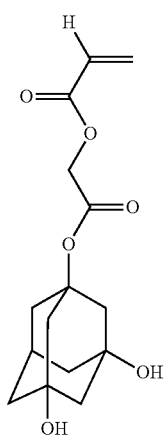

When the resin contains the structural unit derived from the monomer represented by the formula (a2-1), the content of the structural unit derived from the monomer represented by the formula (a2-1) is usually 3 to 45% by mole based on total molar of all the structural units of the resin, and preferably 5 to 40% by mole, and more preferably S to 35% by mole, and still more preferably 5 to 20% by mole.

Examples of the lactone ring of the compound having no acid-labile group and a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and having a lactone ring include the monomers represented by the formulae (a3-1), (a3-2) and (a3-3):

(a3-1)

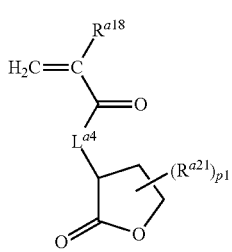

(a3-2)

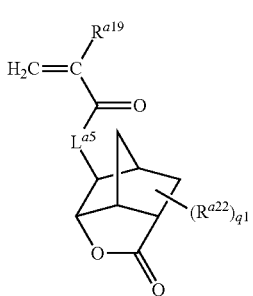

(a3-3)

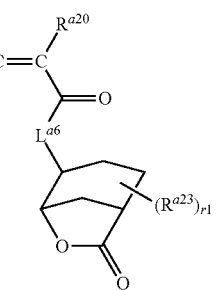

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 alkyl group, $R^{a22}$ and $R^{a23}$ are independently in each occurrence a carboxyl group, a cyano group or a C1-C4 alkyl group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, preferably d1 is 1, and it is more preferred that $L^{a4}$, $L^{a5}$ and $L^{a6}$ are *—O—. $R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the monomer represented by the formula (a3-1) include the monomers described in JP 2010-204646 A, and the monomers represented by the formulae (a3-1-1) to (a3-1-4), (a3-2-1) to (a3-2-4) and (a3-3-1) to (a3-3-4) and the monomers represented by the formulae (a3-1-1) to (a3-1-2) and (a3-2-3) to (a3-2-4) are preferable, and the monomers represented by the formulae (a3-1-1) and (a3-2-3) are more preferable.

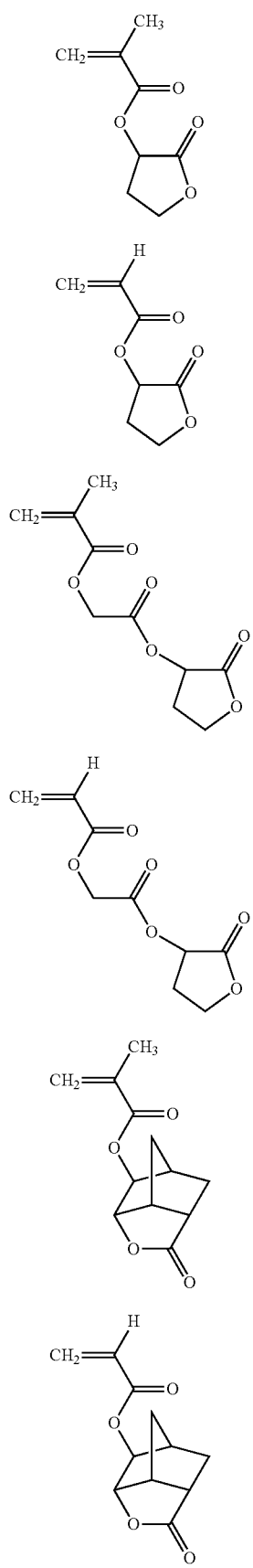
(a3-1-1)
(a3-1-2)
(a3-1-3)
(a3-1-4)
(a3-2-1)
(a3-2-2)
-continued
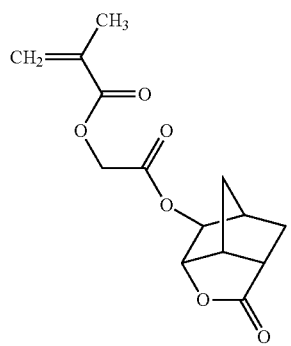 (a3-2-3)
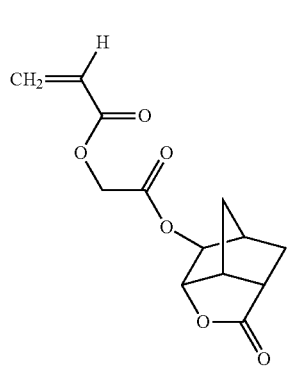 (a3-2-4)
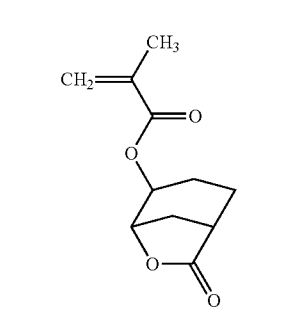 (a3-3-1)
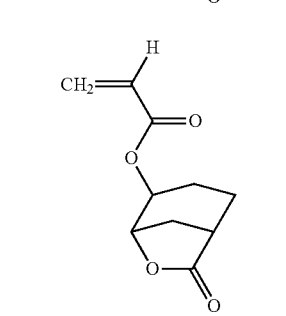 (a3-3-2)
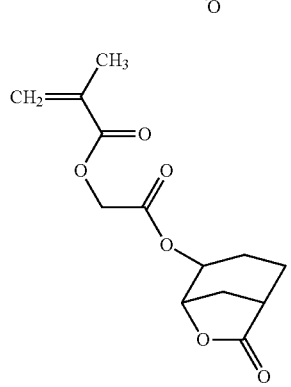 (a3-3-3)

(a3-3-4)

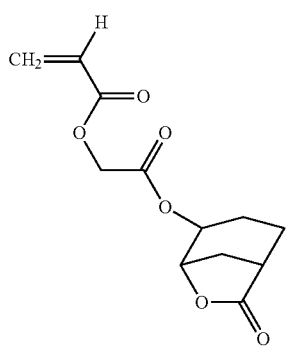

When the resin contains the structural unit derived from the monomer having no acid-labile group and having a lactone ring, the content thereof is usually 5 to 70% by mole based on total molar of all the structural units of the resin, and preferably 10 to 65% by mole and more preferably 10 to 60% by mole.

When the resin contains the structural unit derived from the monomer represented by the formula (a3-1), (a3-2) or (a3-3), the content thereof is usually 5 to 60% by mole based on total molar of all the structural units of the resin, and preferably 5 to 50% by mole and more preferably 10 to 50% by mole.

The resin can contain one or more structural units derived from known monomers other than the above-mentioned monomers.

Preferable resin is a resin containing the structural units derived from the monomer having an acid-labile group and the structural units derived from the monomer having no acid-labile group, and more preferable resin is a resin containing the structural units derived from the monomer having an acid-labile group and the structural units derived from the monomer having one or more hydroxyl groups and/or the monomer having a lactone ring. The monomer having an acid-labile group is preferably the monomer represented by the formula (a1-1) or the monomer represented by the formula (a1-2), and is more preferably the monomer represented by the formula (a1-1). The monomer having one or more hydroxyl groups is preferably the monomer represented by the formula (a2-1), and the monomer having a lactone ring is preferably the monomer represented by the formula (a3-1) or (a3-2).

The resin can be produced according to known polymerization methods such as radical polymerization.

The resin usually has 2,500 or more of the weight-average molecular weight, and preferably 3,000 or more of the weight-average molecular weight. The resin usually has 50,000 or less of the weight-average molecular weight, and preferably has 30,000 or less of the weight-average molecular weight. The weight-average molecular weight can be measured with gel permeation chromatography and can be calculated based the results of the chromatography using standard polystyrene.

The photoresist composition of the present invention usually includes 80% by mass or more of the resin based on sum of solid component.

Next, the acid generator will be illustrated.

The photoresist composition of the present invention contains an acid generator.

The acid generator is a substance which is decomposed to generate an acid by applying a radiation such as a light, an electron beam or the like on the substance itself or on a photoresist composition containing the substance. The acid generated from the acid generator acts on the resin resulting in cleavage of the acid-labile group existing in the resin.

Examples of the acid generator include a nonionic acid generator, an ionic acid generator and the combination thereof. Examples of the nonionic acid generator include an organo-halogen compound, a sulfone compound such as a disulfone, a ketosulfone and a sulfonyldiazomethane, a sulfonate compound such as a 2-nitrobenzylsulfonate, an aromatic sulfonate, an oxime sulfonate, an N-sulfonyloxyimide, a sulfonyloxyketone and diazonaphthoquinone 4-sulfonate. Examples of the ionic acid generator include an onium salt compound such as a diazonium salt, a phosphonium salt, a sulfonium salt and an iodonium salt. Examples of the anion of the onium salt include a sulfonic acid anion, a sulfonylimide anion and a sulfonulmethide anion. The onium salt compound is preferable.

Other examples of the acid generator include acid generators described in JP 63-26653A, JP 55-164824A, JP 62-69263A, JP 63-146038 A, JP 63-163452 A, JP 62-153853 A, JP 63-146029 A, U.S. Pat. Nos. 3,779,778, 3,849,137, DE Patent No. 3914407 and EP Patent No. 126,712.

A fluorine-containing acid generator is preferable.

Preferable examples of the acid generator include a salt represented by the formula (B1):

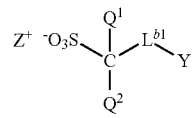

(B1)

wherein $Q^1$ and $Q^2$ each independently represent a fluorine atom or a C1-C6 perfluoroalkyl group, $L^{b1}$ represents a single bond or a C1-C17 saturated divalent hydrocarbon group which can have one or more substituents, and one or more —CH$_2$— in the saturated divalent hydrocarbon group can be replaced by —O— or —CO—, Y represents a C1-C18 alkyl group or a C3-C18 alicyclic hydrocarbon group, and the alkyl group and the cyclic hydrocarbon group can have one or more substituents, and one or more —CH$_2$— in the alkyl group and the cyclic hydrocarbon group can be replaced by —O—, —CO— or —SO$_2$—, and Z* represents an organic cation.

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

Examples of the C1-C17 saturated divalent hydrocarbon group include a C1-C17 alkanediyl group, a monocyclic or polycyclic divalent alicyclic hydrocarbon group and a group formed by combining two or more groups selected from the group consisting of the above-mentioned C1-C17 alkanediyl group and the above-mentioned monocyclic or polycyclic divalent alicyclic hydrocarbon group. Examples of the alkanediyl group include a linear alkanediyl group such as a methylene group, an ethylene group, a propane-1,3-diyl group, a butane-1,4-diyl group, a pentane-1,5-diyl, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, a heptadecane-1,17-diyl group, an ethane-1,1-diyl group, a propane-1,1-diyl group and a propane-2,2-diyl group, a branched chain alkanediyl group formed by replacing one or more hydrogen atom of the above-mentioned linear alkanediyl group by a C1-C4 alkyl group such as a butane-1,3-diyl group, a 2-methylpropane-1,3-diyl group, a 2-methylpropane-1,2-diyl group, a pentane-1,4-diyl group and a 2-methylbutane-1,4-diyl group.

Examples of the monocyclic divalent alicyclic hydrocarbon group include a cyclobutane-1,3-diyl group, a cyclopentane-1,3-diyl group, a cyclohexane-1,4-diyl group and a cyclooctane-1,5-diyl group, and examples of the polycyclic divalent alicyclic hydrocarbon group include a norbornane-1,4-diyl group, a norbornane-2,5-diyl group, an adamantine-1,5-diyl group and an adamantine-2,6-diyl group.

One or more —$CH_2$— in the C1-C17 saturated hydrocarbon group can be replaced by —O— or —CO—.

Examples of the C1-C17 saturated hydrocarbon group in which one or more —$CH_2$— are replaced by —O— or —CO— include *—CO—O-$L^{b2}$-, *—CO—O-$L^{b4}$-CO—O-$L^{b3}$-, *-$L^{b5}$-O—CO—, *$L^{b7}$-O-$L^{b6}$-, *—CO—O-$L^{b8}$-O—, and *—CO—O-$L^{b10}$-O-$L^{b9}$-CO—O—, wherein $L^{b2}$ represents a single bond or a C1-C15 divalent saturated hydrocarbon group, $L^{b3}$ represents a single bond or a C1-C12 divalent saturated hydrocarbon group, $L^{b4}$ represents a single bond or a C1-C13 divalent saturated hydrocarbon group, with proviso that total carbon number of $L^{b3}$ and $L^{b4}$ is 1 to 13, $L^{b5}$ represents a C1-C15 divalent saturated hydrocarbon group, $L^{b6}$ represents a C1-C15 divalent saturated hydrocarbon group, $L^{b7}$ represents a C1-C15 divalent saturated hydrocarbon group, with proviso that total carbon number of $L^{b6}$ and $L^{b7}$ is 1 to 16, $L^{b8}$ represents a C1-C14 divalent saturated hydrocarbon group, $L^{b9}$ represents a C1-C11 divalent saturated hydrocarbon group, $L^{b10}$ represents a C1-C11 divalent saturated hydrocarbon group, with proviso that total carbon number of $L^{b9}$ and $L^{b10}$ is 1 to 12, and * represents a binding position to —C($Q^1$)($Q^2$)-. Among them, preferred is *—CO—O-$L^{b2}$-, and more preferred is *—CO—O-$L^{b2}$- in which $L^{b2}$ is a single bond or —$CH_2$—.

Examples of *—CO—O-$L^{b2}$- include *—CO—O— and *—CO—O—$CH_2$—. Examples of *—CO—O-$L^{b4}$-CO—O-$L^{b3}$- include *—CO—O—$CH_2$—CO—O—, *—CO—O—($CH_2$)$_2$—CO—O—, *—CO—O—($CH_2$)$_3$—CO—O—, *—CO—O—($CH_2$)$_4$—CO—O—, *—CO—O—($CH_2$)$_6$—CO—O—, *—CO—O—($CH_2$)$_8$—CO—O—, *—CO—O—$CH_2$—CH($CH_3$)—CO—O— and *—CO—O—$CH_2$—C($CH_3$)$_2$—CO—O—. Examples of *-$L^{b5}$-O—CO— include *—$CH_2$—O—CO—, *—($CH_2$)$_2$—O—CO—, *—($CH_2$)$_3$—O—CO—, *—($CH_2$)$_4$—O—CO—, *—($CH_2$)$_6$—O—CO— and *—($CH_2$)$_8$—O—CO—. Examples of *-$L^{b7}$-O-$L^{b6}$- include *—$CH_2$—O—$CH_2$—. Examples of *—CO—O-$L^{b8}$-O— include *—CO—O—$CH_2$—O—, *—CO—O—($CH_2$)$_2$—O—, *—CO—O—($CH_2$)$_3$—O—, *—CO—O—($CH_2$)$_4$—O— and followings.

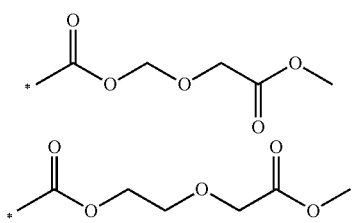

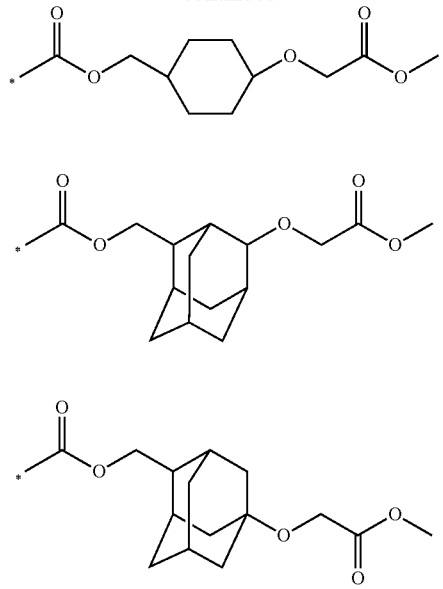

Examples of the substituent in Y include a halogen atom, a hydroxyl group, an oxo group, a glycidyloxy group, a C2-C4 acyl group, a C1-C12 alkoxy group, a C2-C7 alkoxycarbonyl group, a C1-C12 aliphatic hydrocarbon group, a C1-C12 hydroxy-containing aliphatic hydrocarbon group, a C3-C16 saturated cyclic hydrocarbon group, a C6-C18 aromatic hydrocarbon group, a C7-C21 aralkyl group and —($CH_2$)$_{j2}$—O—CO—$R^{b1}$— in which $R^{b1}$ represents a C1-C16 alkyl group, a C3-C16 alicyclic hydrocarbon group or a C6-C18 aromatic hydrocarbon group and j2 represents an integer of 0 to 4. Examples of the halogen atom include a fluorine atom, a chlorine atom, a bromine atom and an iodine atom. Examples of the acyl group include an acetyl group and a propionyl group, and examples of the alkoxy group include a methoxy group, an ethoxy group, a propoxy group, an isopropoxy group and a butoxy group. Examples of the alkoxycarbonyl group include a methoxycarbonyl group, an ethoxycarbonyl group, a propoxycarbonyl group, an isopropoxycarbonyl group and a butoxycarbonyl group. Examples of the alkyl, group include the same as described above. Examples of the hydroxyl-containing aliphatic hydrocarbon group include a hydroxymethyl group. Examples of the C3-C16 alicyclic hydrocarbon group include the same as described above, and examples of the aromatic hydrocarbon group include a phenyl group, a naphthyl group, an anthryl group, a p-methylphenyl group, a p-tert-butylphenyl group and a p-adamantylphenyl group. Examples of the aralkyl group include a benzyl group, a phenethyl group, a phenylpropyl group, a trityl group, a naphthylmethyl group and a naphthylethyl group.

Examples of the C1-C18 alkyl group represented by Y include a methyl group, an ethyl group, a propyl group, an isopropyl group, a butyl group, an isobutyl group, a sec-butyl group, a tort-butyl group, a pentyl group, a neopentyl group, a 1-methylbutyl group, a 2-methylbutyl group, a 1,2-dimethylpropyl group, a 1-ethylpropyl group, a hexyl group, a 1-methylpentyl group, a heptyl group, an octyl group, a 2-ethylhexyl group, a nonyl group, a decyl group, an undecyl group and a dodecyl group, and a C1-C6 alkyl group is preferable.

Examples of the C3-C18 alicyclic hydrocarbon group represented by Y include the groups represented by the formulae (Y1) to (Y29):

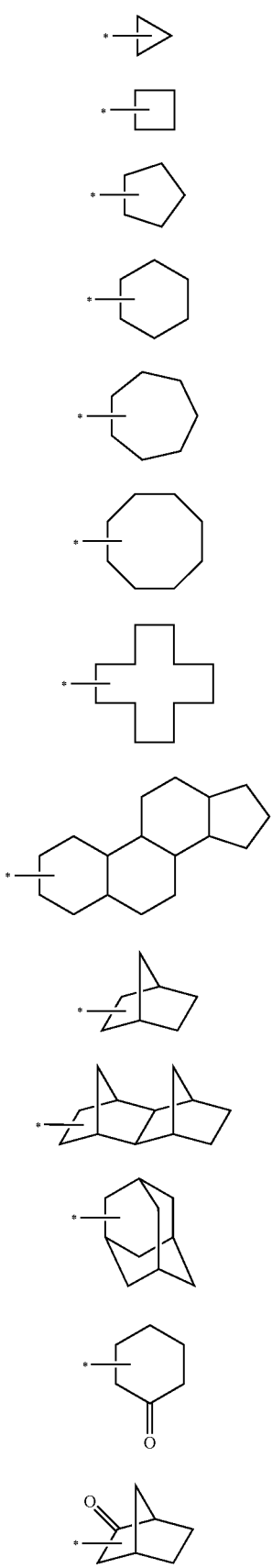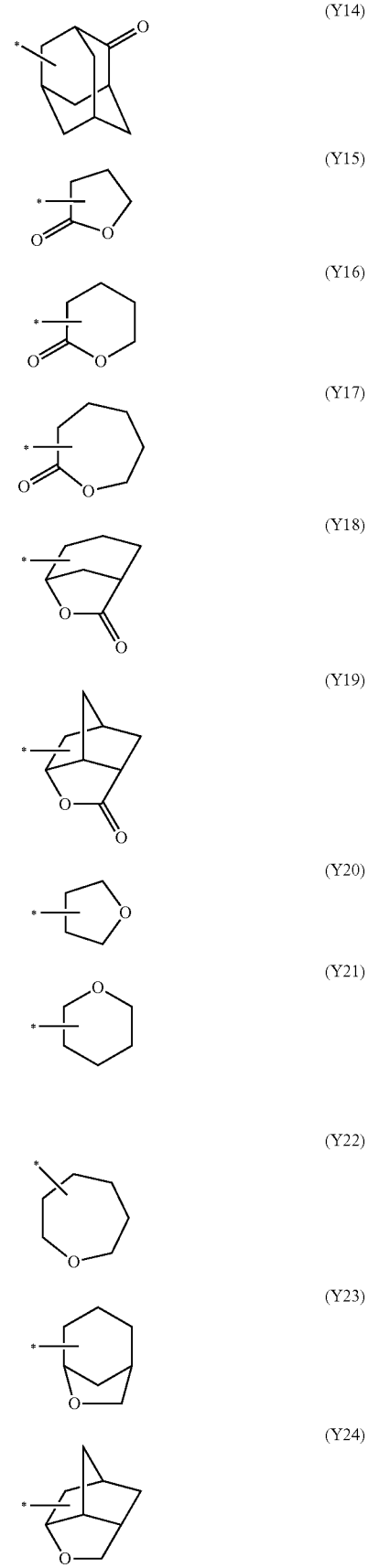

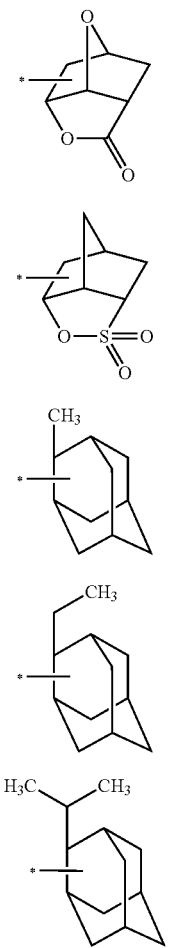

(Y25)
(Y26)
(Y27)
(Y28)
(Y29)

Among them, preferred are the groups represented by the formulae (Y1) to (Y19) and (Y27) to (Y29), and more preferred are the groups represented by the formulae (Y11), (Y14), (Y15), (Y19), (Y27), (Y28) and (Y29), and still more preferred are the groups represented by the formulae (Y11) and (Y14).

Examples of Y having one or more substituents include the followings:

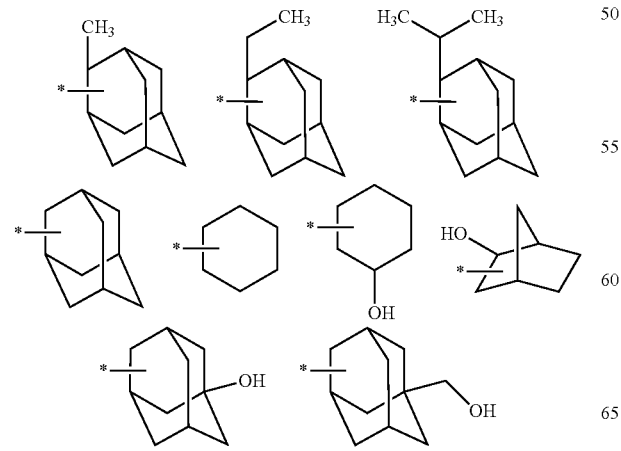

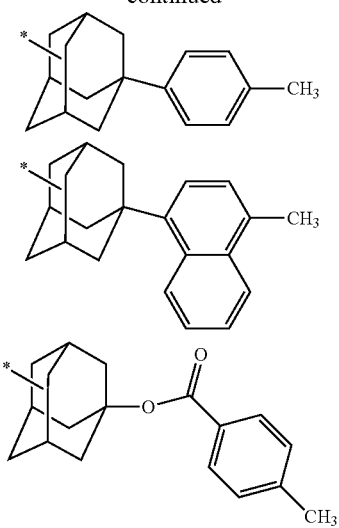

When Y is an alkyl group and $L^{b1}$ is a C1-C17 divalent aliphatic hydrocarbon group, one or more —CH$_2$— in the C1-C17 divalent aliphatic hydrocarbon group are preferably replaced by —O— or —CO— and —CH$_2$— in the alkyl group is not replaced by —O— or —CO—.

Y is preferably a C3-C18 alicyclic hydrocarbon group which can have one or more substituents, and more preferably an adamantyl group which can have one or more substituents, and still more preferably an adamantyl group, a hydroxyadamantyl group or an oxoadamantyl group.

Among the sulfonic acid anions of the acid generator represented by the formula (B1), preferred are anions represented by the formulae (b1-1-1) to (b1-1-9).

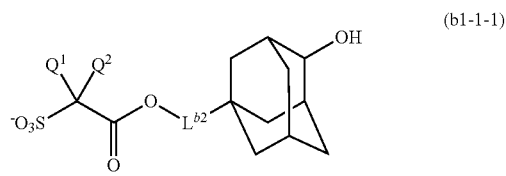

(b1-1-1)

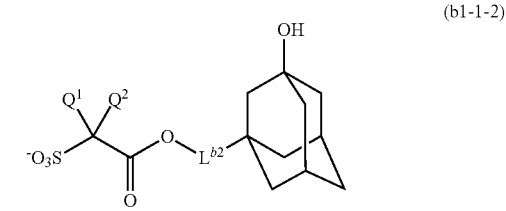

(b1-1-2)

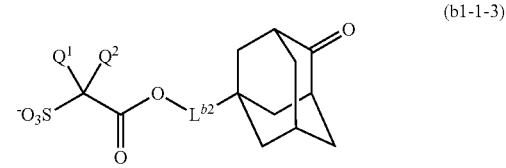

(b1-1-3)

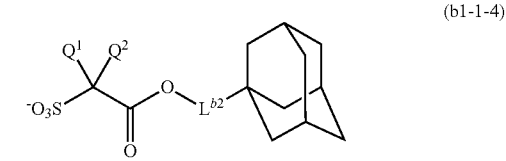

(b1-1-4)

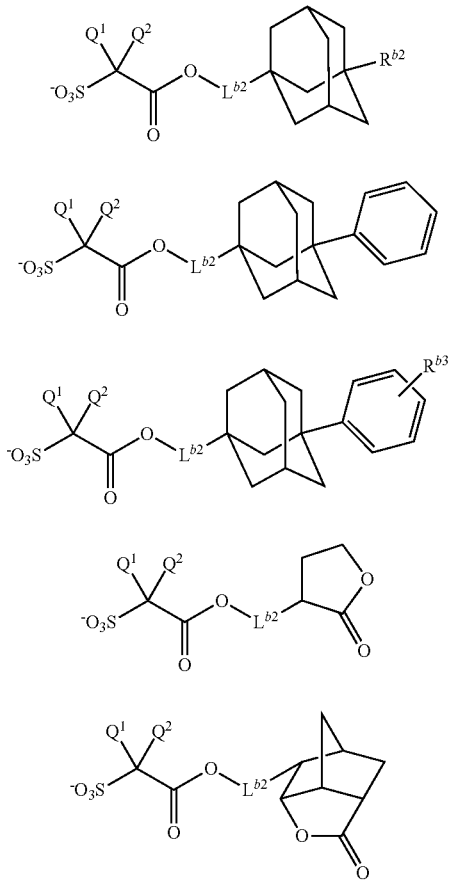

(b1-1-5)
(b1-1-6)
(b1-1-7)
(b1-1-8)
(b1-1-9)

wherein $Q^1$, $Q^2$ and $L^{b2}$ are the same as defined above, and $R^{b2}$ and $R^{b3}$ each independently represent the same as the substituent of the aliphatic hydrocarbon group or the alicyclic hydrocarbon group represented by Y. It is preferred that $R^{b2}$ and $R^{b3}$ each independently represent a C1-C4 aliphatic hydrocarbon group or a hydroxyl group, and it is more preferred that $R^{b2}$ and $R^{b3}$ each independently represent a methyl group or a hydroxyl group.

Examples of the cation part represented by $Z^+$ include an organic onium cation such as a organic sulfonium cation, an organic iodonium cation, an organic ammonium cation, a benzothiazolium cation and an organic phosphonium cation, and an organic sulfonium cation and an organic iodonium cation are preferable, and an arylsulfonium cation is more preferable. In this specification, "arylsulfonium cation" means a sulfonium cation having at least one aryl group.

Preferable examples of the cation part represented by $Z^+$ include the cations represented by the formulae (b2-1) to (b2-4):

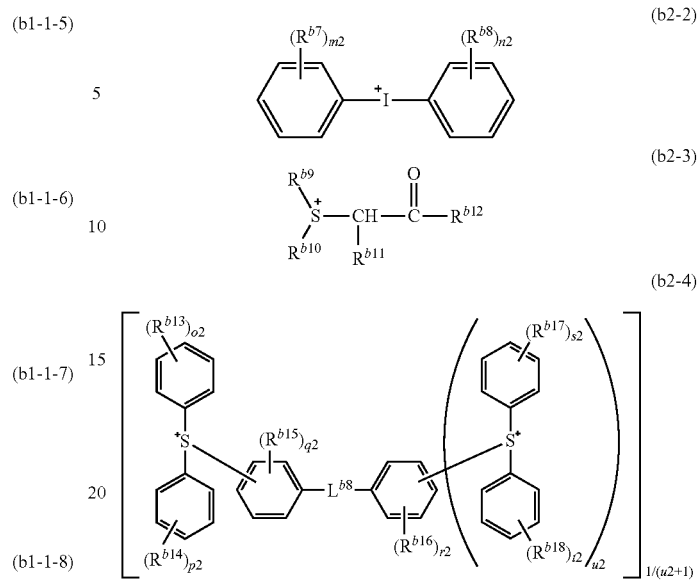

(b2-1)
(b2-2)
(b2-3)
(b2-4)

wherein $R^{b4}$, $R^{b5}$ and $R^{b6}$ each independently represent a C1-C30 alkyl group which can have one or more substituents selected from the group consisting of a hydroxyl group, a C1-C12 alkoxy group and a C6-C18 aromatic hydrocarbon group, a C3-C18 alicyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C18 aliphatic hydrocarbon group, a C3-C18 alicyclic hydrocarbon group or a C1-C12 alkoxy group, $R^{b7}$ and $R^{b8}$ are independently in each occurrence a hydroxyl group, a C1-C12 alkyl group or a C1-C12 alkoxy group, m2 and n2 independently represents an integer of 0 to 5, $R^{b9}$ and $R^{b10}$ each independently represent a C1-C18 alkyl group or a C3-C18 alicyclic hydrocarbon group, or $R^{b9}$ and $R^{b10}$ are bonded to form a C2-C11 divalent acyclic hydrocarbon group which forms a ring together with the adjacent $S^+$, and one or more —$CH_2$— in the divalent acyclic hydrocarbon group may be replaced by —CO—, —O— or —S—, and $R^{b11}$ represents a hydrogen atom, a C1-C18 alkyl group, a C3-C18 alicyclic hydrocarbon group or a C6-C18 aromatic hydrocarbon group, $R^{b12}$ represents a C1-C12 alkyl group, a C3-C18 alicyclic hydrocarbon group or a C6-C18 aromatic hydrocarbon group and the aromatic hydrocarbon group can have one or more substituents selected from the group consisting of a C1-C12 alkyl group, a C1-C12 alkoxy group, a C3-C18 alicyclic hydrocarbon group and a C2-C13 acyloxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —$CH_2$— in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ each independently represent a hydroxyl group, a C1-C12 alkyl group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

The alkyl group represented by $R^{b9}$ to $R^{b11}$ has preferably 1 to 12 carbon atoms. The alicyclic hydrocarbon group represented by $R^{b9}$ to $R^{b11}$ has preferably 4 to 12 carbon atoms.

Examples of the alkyl group and the aromatic hydrocarbon group include the same as described above. Preferable examples of the alkyl group include a C1-C12 alkyl group such as a methyl group, an ethyl group, a propyl group, an isopropyl group, a butyl group, a sec-butyl group, a tent-butyl group, a pentyl group, a hexyl group, an octyl group and a 2-ethylhexyl group. Examples of the alicyclic hydrocarbon group include a cycloalkyl group such as a cyclopentyl group, a cyclohexyl group, a cycloheptyl group and a cyclooctyl group, and polycyclic alicyclic hydrocarbon group such as a decahydronaphthyl group, an adamantyl group, a norbornyl group, a methylnorbornyl group and the following groups.

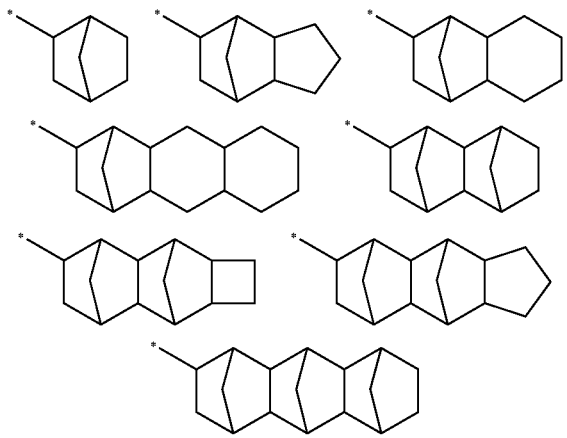

Preferable examples of the alicyclic hydrocarbon group include a cyclopropyl group, a cyclobutyl group, a cyclopentyl group, a cyclohexyl group, a cycloheptyl group, a cyclodecyl group, a 2-alkyladamantan-2-yl group, a 1-(adamantan-1-yl)alkan-1-yl group and an isobornyl group.

Examples of the aromatic group include an aryl group such as a phenyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group, a 2-methyl-6-ethylphenyl group and a naphthyl group. Preferred are a phenyl group, a p-methylphenyl group, a p-ethylphenyl group, a p-tert-butylphenyl group, a p-cyclohexylphenyl group, a p-methoxyphenyl group, a biphenyl group and a naphthyl group.

Examples of the aliphatic hydrocarbon group having an aromatic hydrocarbon group include a benzyl group, a phenylethyl group, a phenylpropyl group, a trityl group, a naphthylmethyl group and a naphthylethyl group, and a benzyl group is preferable. Examples of the alkoxy group include a methoxy group, an ethoxy group, a propoxy group, an isopropoxy group, a butoxy group, a sec-butoxy group, a tortbutoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group, and a C1-C12 alkoxy group is preferable.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent S+ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

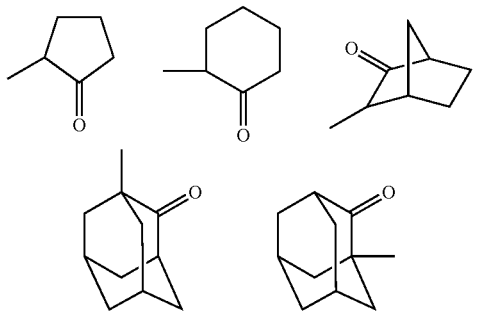

A C1-C5 divalent acyclic hydrocarbon group is preferable.

Among the above-mentioned cations, preferred is the cation represented by the formula (b2-1), and more preferred is the cation represented by the formula (b2-1-1). A triphenylsulfonium cation and a tritolylsulfonium cation are especially preferable.

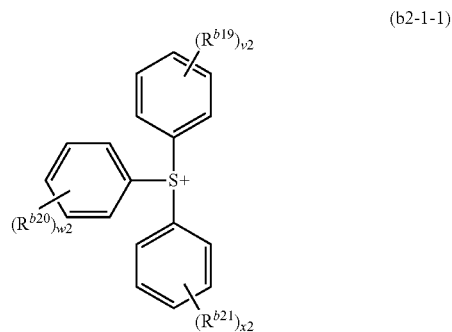

(b2-1-1)

wherein $R^{b19}$, $R^{b20}$ and $R^{b21}$ are independently in each occurrence a halogen atom, a hydroxyl group, a C1-C18 alkyl group, a C3-C18 alicyclic hydrocarbon group or a C1-C12 alkoxy group, and one or more hydrogen atoms of the alkyl group can be replaced by a hydroxyl group, a C1-C12 alkoxy group or a C6-C18 aromatic hydrocarbon group, and one or more hydrogen atoms of the alicyclic hydrocarbon group can be replaced by a halogen atom, a glycidyloxy group or a C2-C4 acyl group, and v2, w2 and x2 independently each represent an integer of 0 to 5.

The alkyl group has preferably 1 to 12 carbon atoms, and the alicyclic hydrocarbon group has preferably 4 to 18 carbon atoms, and v2, w2 and x2 independently each preferably represent 0 or 1.

It is preferred that $R^{b19}$, $R^{b20}$ and $R^{b21}$ are independently in each occurrence a halogen atom, a hydroxyl group, a C1-C12 alkyl group or a C1-C12 alkoxy group and v2, w2 and x2 independently each represent an integer of 0 to 5, and it is more preferred that $R^{b19}$, $R^{b20}$ and $R^{b21}$ are independently in each occurrence a fluorine atom, a hydroxyl group, a C1-C12 alkyl group or a C1-C12 alkoxy group, and v2, w2 and x2 independently each preferably represent 0 or 1.

Examples of the cations represented by the formulae (b2-1) to (B2-4) and (b2-1-1) include the cations described in JP 2010-204646 A.

Examples of the salt represented by the formula (B1) include a salt wherein the anion part is any one of the above-mentioned anion and the cation part is any one of the above-mentioned cation. Preferable examples of the salt include a combination of any one of anions represented by the formulae (b1-1-1) to (b1-1-9) and the cation represented by the formulae (b2-1-1), and a combination of any one of anions represented by the formulae (b1-1-3) to (b1-1-5) and the cation represented by the formulae (b2-3).

The salt represented by the formulae (B1-1) to (B1-20) are preferable, and the salt represented by the formulae (B1-1), (B1-2), (B1-3), (B1-6), (B1-7), (B1-11), (B1-12), (B1-13) and (B1-14) which contain a triphenylsulfonium cation or a tritolylsulfonium cation are more preferable.

(B1-1)

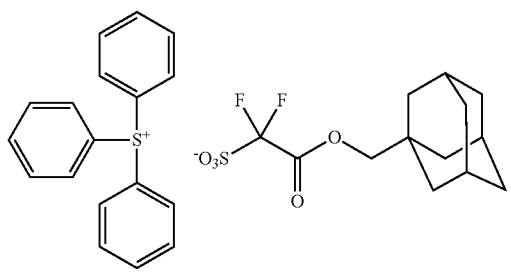

(B1-2)

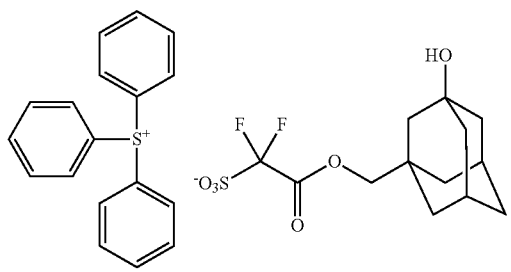

(B1-3)

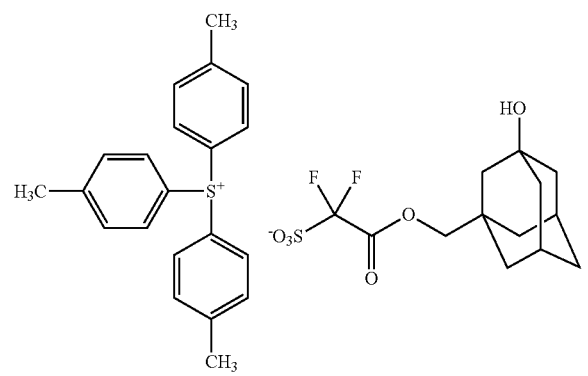

(B1-4)

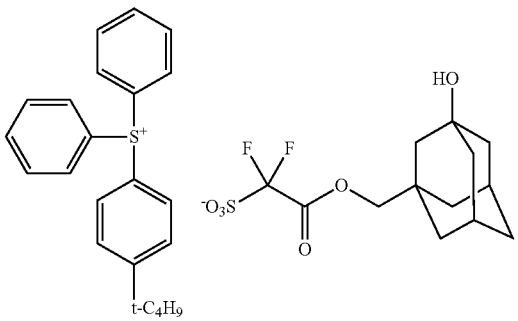

(B1-5)

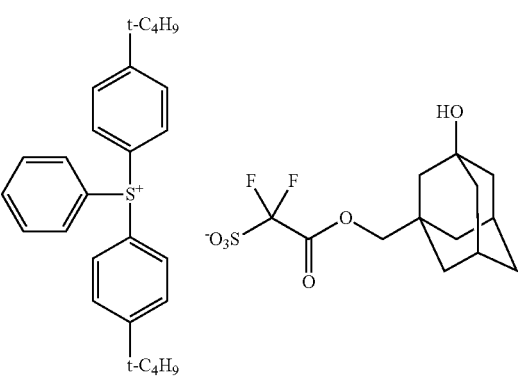

(B1-6)

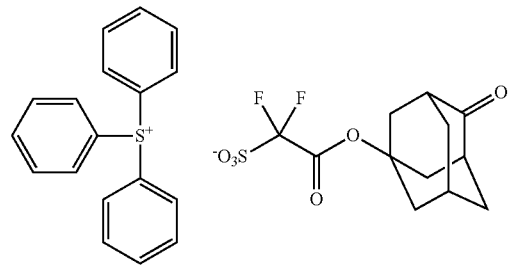

(B1-7)

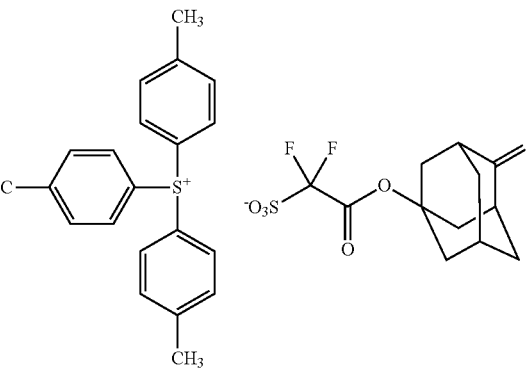

(B1-8)
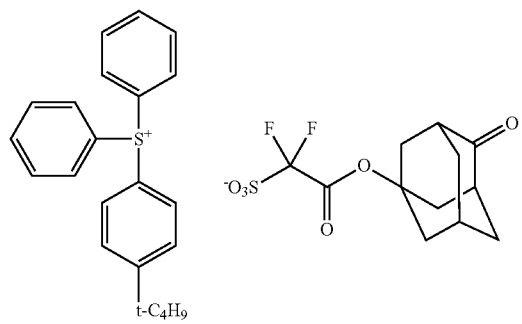
(B1-9)
(B1-10)
(B1-11)
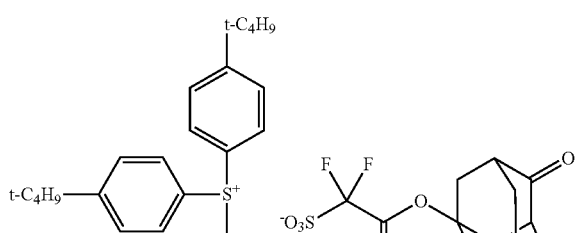
(B1-12)
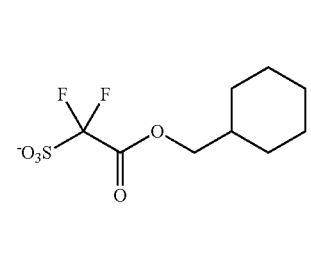
(B1-13)
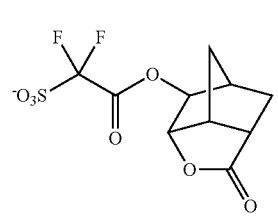
(B1-14)
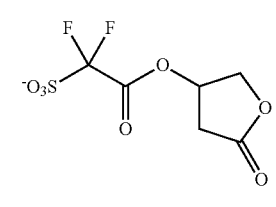
(B1-15)
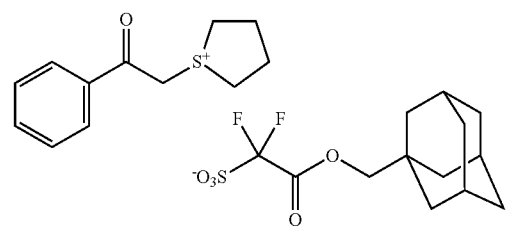
(B1-16)
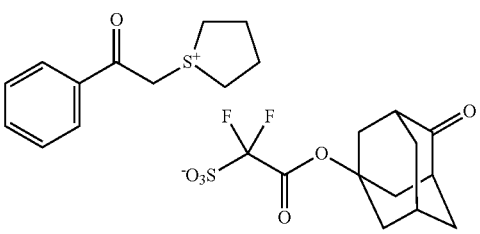
(B1-17)
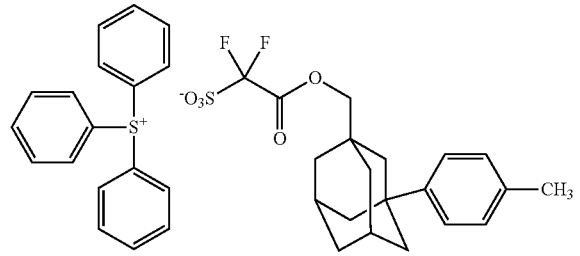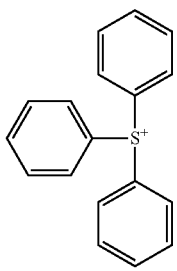

(B1-18)

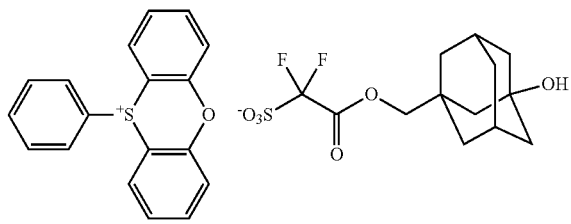

(B1-19)

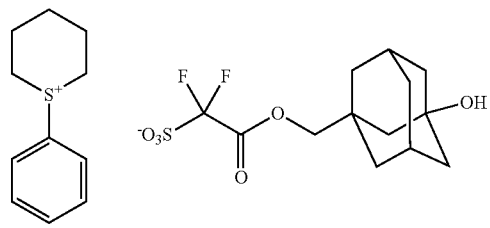

(B1-20)

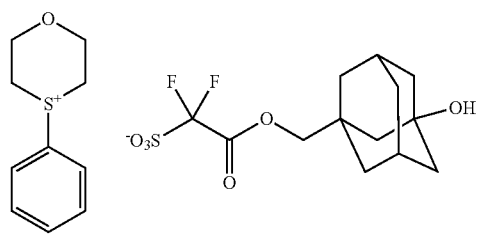

Two or more kinds of the acid generator can be used in combination.

The content of the acid generator is usually 1 part by mass or more and preferably 3 parts by mass or more per 100 parts by mass of the resin component, and 30 parts by mass or less and preferably 25 parts by mass or less per 100 parts by mass of the resin component.

The photoresist composition of the present invention can contain one or more basic compounds, and the content of the basic compound is usually 0.01 to 5% by mass based on solid component, preferably 0.01 to 33 by mass, and more preferably 0.01 to 1% by mass. The basic compound has the property that it can trap an acid, especially an acid generated from the acid generator by applying a radiation.

The basic compound is preferably a basic nitrogen-containing organic compound, and examples thereof include an ammonium salt and an amine compound such as an aliphatic amine and an aromatic amine. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2):

(C2)

$$Ar^{c1}-N\begin{matrix}R^{c5}\\ \\R^{c6}\end{matrix}.$$

wherein $Ar^{c1}$ represents an aromatic hydrocarbon group, and $R^{c5}$ and $R^{c6}$ each independently represent a hydrogen atom, a C1-C6 alkyl group, a C5-C10 alicyclic hydrocarbon group or a C6-C10 aromatic hydrocarbon group, and the alkyl group and the alicyclic hydrocarbon group can have one or more substituents selected from the group consisting of a hydroxyl group, an amino group, an amino group having one or two C1-C4 alkyl groups and a C1-C6 alkoxy group, and the aromatic hydrocarbon group can have one or more substituents selected from the group consisting of a C1-C6 alkyl group, a C5-C10 alicyclic hydrocarbon group, a C6-C10 aromatic hydrocarbon group and a C1-C6 alkoxy group.

As the aromatic amine represented by the formula (C2), an amine represented by the formula (C2-1):

(C2-1)

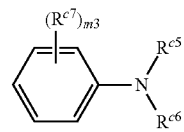

wherein $R^{c5}$ and $R^{c6}$ are the same as defined above, and $R^{c7}$ is independently in each occurrence a C1-C6 alkyl group, a C1-C6 alkoxy group, a C5-C10 alicyclic hydrocarbon group or a C6-C10 aromatic hydrocarbon group, and m3 represents an integer of 0 to 3, is preferable. The alicyclic hydrocarbon group is preferably a cycloalkyl group.

An ammonium salt represented by the formula (02-2):

(C2-2)

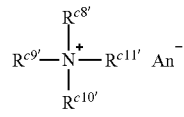

wherein $R^{c8\prime}$, $R^{c9\prime}$, $R^{c10\prime}$ and $R^{c11\prime}$ each independently represent an alkyl group, an alicyclic hydrocarbon group or an aromatic hydrocarbon group, and the alkyl group, the alicyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and $An^-$ represents $OH^-$, is also preferable. The alkyl group has preferably 1 to 6 carbon atoms, and the alicyclic hydrocarbon group has preferably 3 to 6 carbon atoms, and the aromatic hydrocarbon group has preferably 6 to 10 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2, 6-diisopropylaniline Examples of the ammonium salt represented by the formula (C2-2) include tetramethylammonium hydroxide and tetrabutylammonium hydroxide.

Other examples of the basic compound include amines represented by the formulae (C3) to (C11):

(C3)

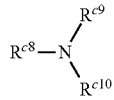

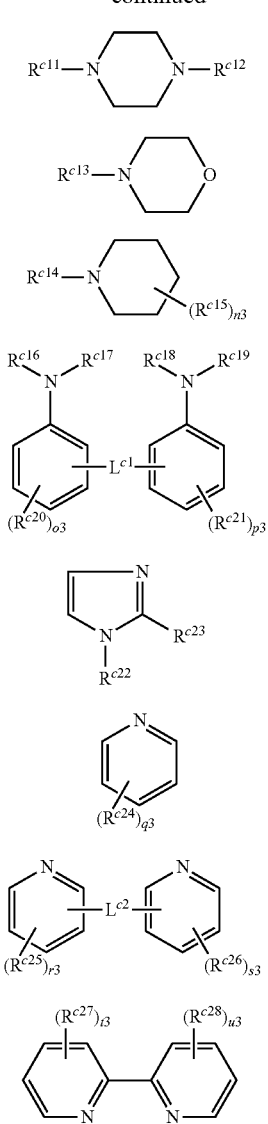

wherein $R^{c8}$, $R^{c20}$, $R^{c21}$, and $R^{c23}$ to $R^{c28}$ each independently represent an alkyl group, an alkoxy group, an alicyclic hydrocarbon group or an aromatic hydrocarbon group, and the alkyl group, the alkoxy group, the alicyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$, $R^{c10}$, $R^{c11}$ to $R^{c14}$, $R^{c16}$ to $R^{c19}$, and $R^{c22}$ each independently represents a hydrogen atom, an alkyl group, an alicyclic hydrocarbon group or an aromatic hydrocarbon group, and the alkyl group, the alicyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c15}$ is independently in each occurrence an alkyl group, an alicyclic hydrocarbon group or an alkanoyl group, $L^{c1}$ and $L^{c2}$ each independently represents a divalent aliphatic hydrocarbon group, —CO—, —C(=NH)—, —C(=NR$^{c3}$)—, —S—, —S—S— or a combination thereof and $R^{c3}$ represents a C1-C4 alkyl group, O3 to u3 each independently represents an integer of 0 to 3 and n3 represents an integer of 0 to 8.

The alkyl group has preferably 1 to 6 carbon atoms, and the alicyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

The photoresist composition of the present invention usually contains one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by mass or more, preferably 92% by mass or more preferably 94% by mass or more based on total amount of the photoresist composition of the present invention. The amount of the solvent is usually 99.9% by mass or less based on total amount of the photoresist composition of the present invention, and preferably 99% by mass or less. The photoresist composition containing a solvent can be preferably used for producing a thin layer photoresist pattern.

The photoresist composition of the present invention can contain, if necessary, a small amount of various additives such as a sensitizer, a dissolution inhibitor, other polymers, a surfactant, a stabilizer and a dye as long as the effect of the present invention is not prevented.

The photoresist composition of the present invention is useful for a chemically amplified photoresist composition.

A photoresist pattern can be produced by the following steps (1) to (5)

(1) a step of applying the photoresist composition of the present invention on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having 0.01 to 0.2 μm of a pore size before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser). Other examples of the exposure source include EUV (extreme ultraviolet) and EB (electron beam).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammonium hydroxide (commonly known as "choline") is often used. After development, the photoresist pattern formed is preferably washed with ultrapure water, and the remained water on the photoresist pattern and the substrate is preferably removed.

The photoresist composition of the present invention provides a photoresist pattern in a good focus margin, and therefore, the photoresist composition of the present invention is suitable for ArF excimer laser lithography, KrF excimer laser lithography, EUV (extreme ultraviolet) lithography, EUV immersion lithography and EB (electron beam) lithography, and the photoresist composition of the present invention is especially suitable for immersion lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [Column (Three Columns with guard column): TSKgel Multipore HXL-M, manufactured by TOSOH CORPORATION, Solvent: Tetrahydrofuran, Flow rate: 1.0 mL/min., Detector: RI detector, Column temperature: 40° C., Injection volume: 100 μL] using standard polystyrene, manufactured by TOSOH CORPORATION, as a standard reference material. The content ratio of the structural unit derived from each monomer in the resin was calculated based on the amount of the unreacted monomers in the reaction mixture, which was measured by liquid chromatography analysis.

Example 1

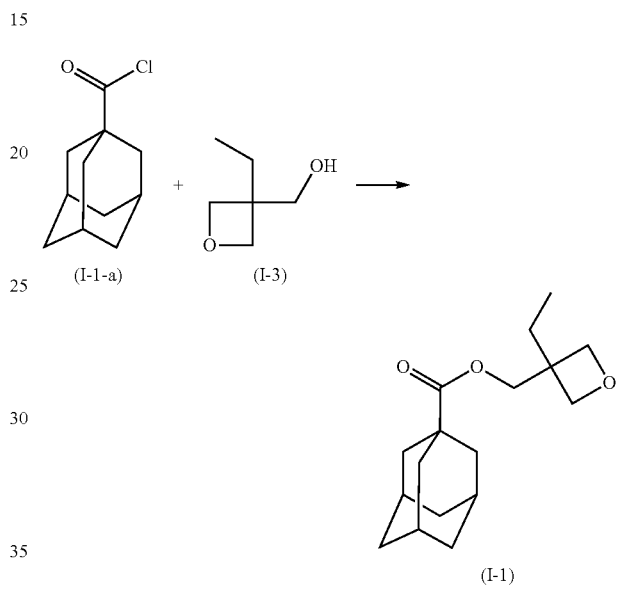

Ten (10) parts of a compound represented by the formula (I-1-a), 6.14 parts of a compound represented by the formula (I-3) available from Tokyo Chemical Industry Co., Ltd., and 120 parts of chloroform were mixed. The resultant mixture was stirred at 23° C. for 30 minutes, and then, 4.78 parts of pyridine was added thereto at 23° C. The mixture obtained was stirred at 23° C. for 12 hours. To the reaction mixture obtained, added was 40 parts of ion-exchanged water. The mixture was stirred and then, separated. This washing was repeated five times. The organic layer obtained was concentrated. The residue was purified with column chromatography (silica gel 60-200 mesh available from Merck KGaA, Developering solvent: heptane/ethyl acetate=2/1) to obtain 11.58 parts of a compound represented by the formula (I-1).

MASS: 278.2

Examples 2

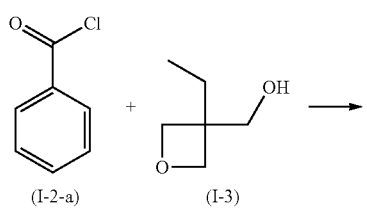

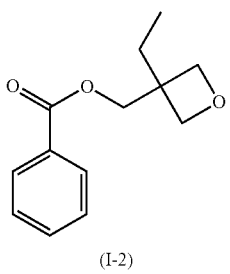

(I-2)

Ten (10) parts of a compound represented by the formula (I-2-a), 8.68 parts of a compound represented by the formula (I-3) available from Tokyo Chemical Industry Co., Ltd., and 120 parts of chloroform were mixed. The resultant mixture was stirred at 23° C. for 30 minutes, and then, 6.75 parts of pyridine was added thereto at 23° C. The mixture obtained was stirred at 23° C. for 12 hours. To the reaction mixture obtained, added was 40 parts of ion-exchanged water. The mixture was stirred and then, separated. This washing was repeated five times. The organic layer obtained was concentrated to obtain 15.42 parts of a compound represented by the formula (I-2).

MASS: 220.1 times. The organic layer obtained was concentrated, and to the residue obtained, 100 parts of tert-butyl methyl ether was added. The resultant mixture was stirred and filtrated. The solid obtained was dried to obtain 12.05 parts of a compound represented by the formula (I-4-c).

Ten (10) parts of the compound represented by the formula (I-4-c), 4.41 parts of a compound represented by the formula (I-3) available from Tokyo Chemical Industry Co., Ltd., and 40 parts of acetone were mixed. The resultant mixture was stirred at 23° C. for 30 minutes, and then, 0.25 part of potassium carbonate was added thereto at 23° C. The mixture obtained was stirred at 23° C. for 4 hours. To the reaction mixture obtained, added were an aqueous solution prepared by dissolving 0.46 part of oxalic acid in 30 parts of ion-exchanged water and 100 parts of chloroform. The mixture was stirred and then, separated. The organic layer was washed six times with 30 parts of ion-exchanged water. The organic layer obtained was concentrated to obtain 10.84 parts of a compound represented by the formula (I-4).

MASS: 324.2

Example 3

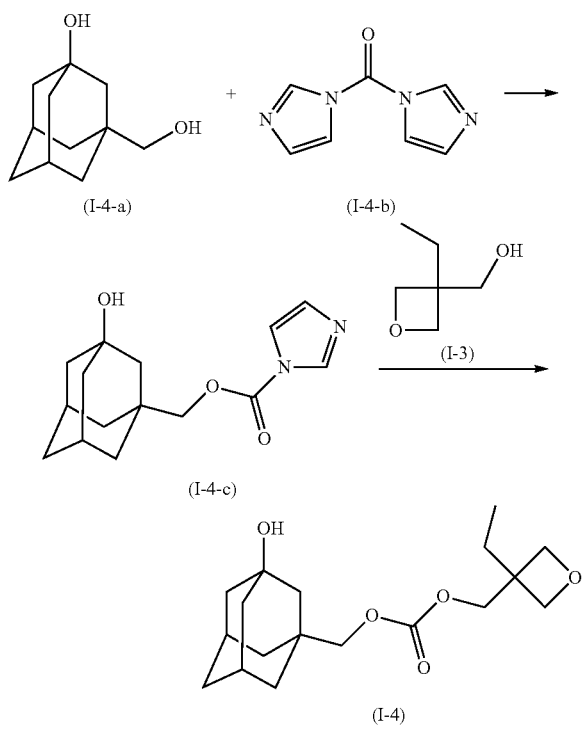

Ten (10) parts of a compound represented by the formula (I-4-a) and 70.00 parts of dichloromethane were mixed. To the mixture obtained, added was 9.79 parts of a compound represented by the formula (I-4-b) available from Tokyo Chemical Industry Co., Ltd. at 23° C. The resultant mixture was stirred at 23° C. for 1 hour. To the mixture obtained, added was 30 parts of ion-exchanged water. The mixture was stirred and then, separated. This washing was repeated five Example 4

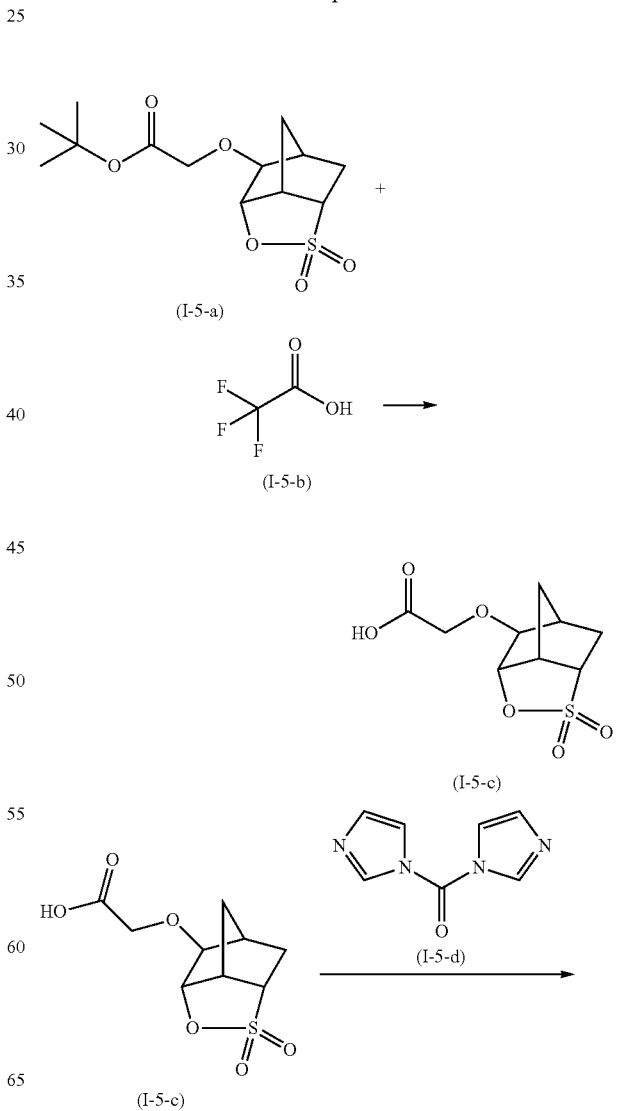

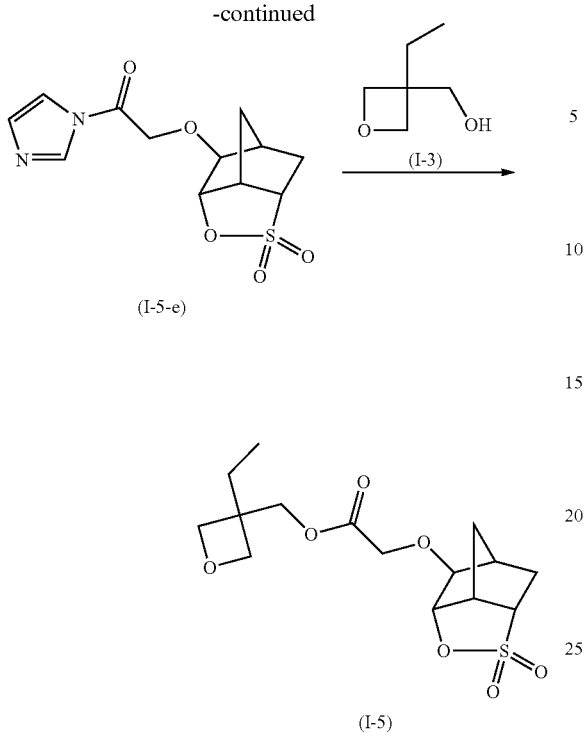

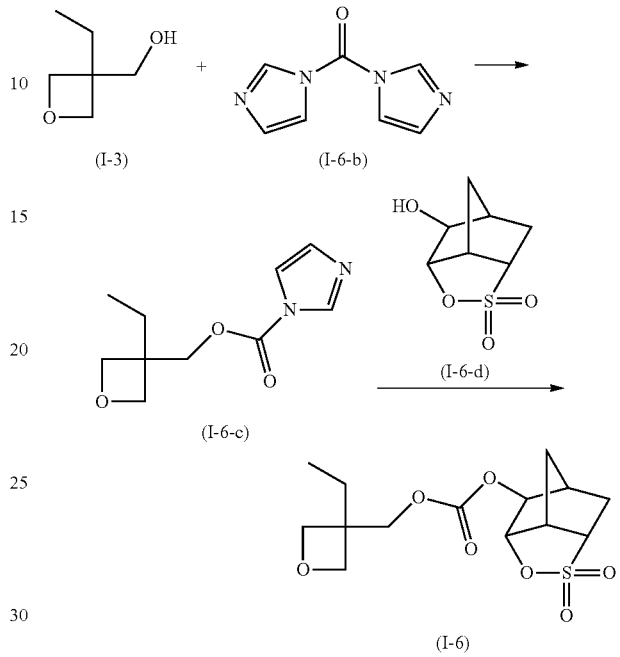

To the reactor, added were 140 parts of chloroform and 14.00 parts of a compound represented by the formula (I-5-a) which was available from Idemitsu and of which trade name was "NSTABu". The resultant mixture was stirred at 23° C. for 30 minutes, and then, 52.45 parts of a compound represented by the formula (I-5-b) was added dropwise thereto. The mixture obtained was stirred at 23° C. for 1 hour, and then, 52.45 parts of a compound represented by the formula (I-5-b) was added dropwise thereto. The resultant mixture was stirred at 23° C. for 2 hours, and then, 52.45 parts of a compound represented by the formula (I-5-b) was added dropwise thereto. The mixture obtained was stirred at 23° C. for 1 hour. The reaction mixture obtained was concentrated. To the residue, added was 20 parts of chloroform. The mixture obtained was stirred and then, concentrated. To the residue, added was 30 parts of heptane The resultant mixture was stirred for 30 minutes, and then, filtrated to obtain 11.19 parts of a compound represented by the formula (I-5-c).

Eight (8) parts of the compound represented by the formula (I-5-c) and 96. 00parts of dichloromethane were mixed. To the mixture obtained, added was 5.49 parts of a compound represented by the formula (I-5-d) available from Tokyo Chemical Industry Co., Ltd. at 23° C. The resultant mixture was stirred at 23° C. for 1 hour to obtain a solution containing a compound represented by the formula (I-5-e).

To the solution containing a compound represented by the formula (I-5-e), added was 3.74 parts of a compound represented by the formula (I-3) available from Tokyo Chemical Industry Co., Ltd., and then, the resultant mixture was stirred at 23° C. for 2 hours. To the mixture obtained, added was 30 parts of ion-exchanged water. The mixture was stirred and then, separated. The organic layer obtained was washed five times with 30 parts of ion-exchanged water. The organic layer obtained was concentrated to obtain 9.85 parts of a compound represented by the formula (I-5).

MASS: 346.1

Example 5

Ten (10) parts of a compound represented by the formula (I-3) and 70.00 parts of dichloromethane were mixed. To the mixture obtained, added was 15.37 parts of a compound represented by the formula (I-6-b) available from Tokyo Chemical Industry Co., Ltd. at 23° C. The resultant mixture was stirred at 23° C. for 3 hours to obtain a solution containing a compound represented by the formula (I-6-c).

To the solution containing a compound represented by the formula (I-6-c), added was 16.38 parts of a compound represented by the formula (I-6-d). The resultant mixture was stirred at 23° C. for 3 hours. An aqueous solution prepared by dissolving 0.5 part of oxalic acid in 30 pats of ion-exchanged water was added to the reaction mixture obtained. The resultant mixture was stirred and then, separated. To the organic layer, added was 30 parts of ion-exchanged water. The resultant mixture was stirred and then, separated. This washing was repeated five times. The organic layer obtained was concentrated to obtain 18.42 parts of a compound represented by the formula (I-6).

MASS: 332.1

Example 6

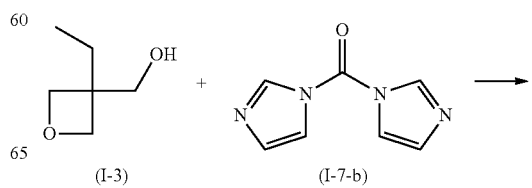

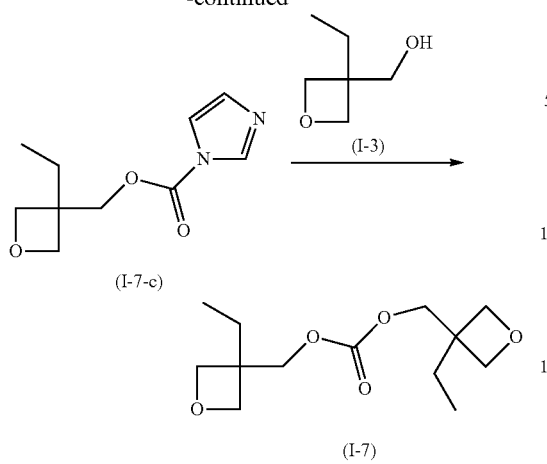

Ten (10) parts of a compound represented by the formula (I-3) and 70.00 parts of dichloromethane were mixed. To the mixture obtained, added was 15.37 parts of a compound represented by the formula (I-7-b) available from Tokyo Chemical Industry Co., Ltd. at 23° C. The resultant mixture was stirred at 23° C. for 3 hours to obtain a solution containing a compound represented by the formula (I-7-c).

To the solution containing a compound represented by the formula (I-7-c), added was 10.00 parts of a compound represented by the formula (I-3). The resultant mixture was stirred at 23° C. for 3 hours. An aqueous solution prepared by dissolving 0.5 part of oxalic acid in 30 pats of ion-exchanged water was added to the reaction mixture obtained. The resultant mixture was stirred and then, separated. To the organic layer, added was 30 parts of ion-exchanged water. The resultant mixture was stirred and then, separated. This washing was repeated five times. The organic layer obtained was concentrated to obtain 12.69 parts of a compound represented by the formula (I-7).

MASS: 258.2

Example 7

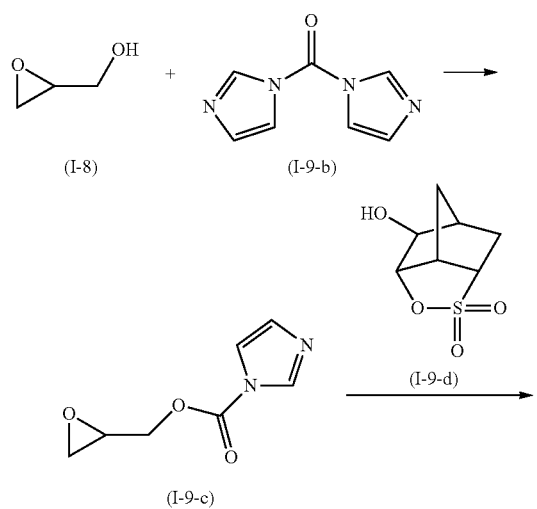

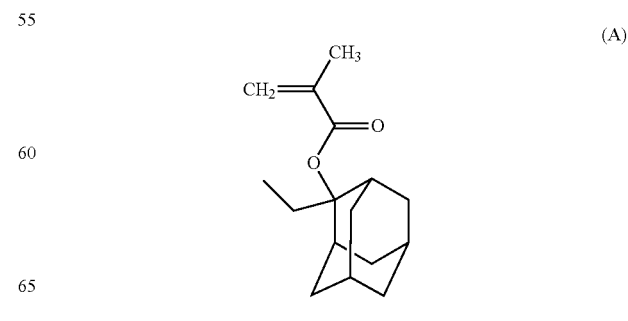

Six point three eight (6.38) parts of a compound represented by the formula (I-8) and 50.00 parts of dichloromethane were mixed. To the mixture obtained, added was 15.37 parts of a compound represented by the formula (I-9-b) available from Tokyo Chemical Industry Co., Ltd. at 23° C. The resultant mixture was stirred at 23° C. for 3 hours to obtain a solution containing a compound represented by the formula (I-9-c).

To the solution containing a compound represented by the formula (I-9-c), added was 16.38 parts of a compound represented by the formula (I-9-d). The resultant mixture was stirred at 23° C. for 3 hours. An aqueous solution prepared by dissolving 0.5 part of oxalic acid in 30 pats of ion-exchanged water was added to the reaction mixture obtained. The resultant mixture was stirred and then, separated. To the organic layer, added was 30 parts of ion-exchanged water. The resultant mixture was stirred and then, separated. This washing was repeated five times. The organic layer obtained was concentrated to obtain 16.67 parts of a compound represented by the formula (I-9).

MASS: 290,1

In Resin Synthesis Examples, monomers represented by the formulae (A) to (G) were used. The monomer represented by the formula (A) is called as Monomer (A). The monomer represented by the formula (B) is called as Monomer (B). The monomer represented by the formula (C) is called as Monomer (C). The monomer represented by the formula (D) is called as Monomer (D). The monomer represented by the formula (E) is called as Monomer (E). The monomer represented by the formula (F) is called as Monomer (F). The monomer represented by the formula (G) is called as Monomer (G).

-continued

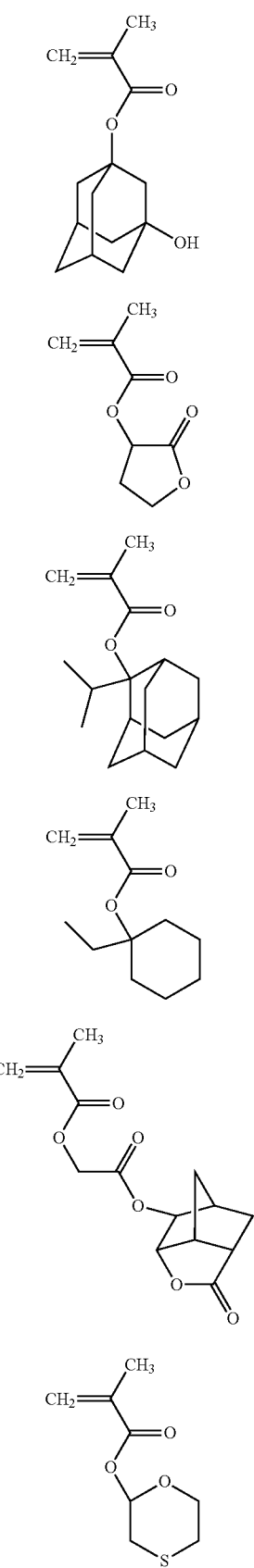

(B)

(C)

(D)

(E)

(F)

(G)

Resin Synthesis Example 1

Monomer (D), Monomer (E), Monomer (B), Monomer (C) and Monomer (F) were mixed at a molar ratio of 30:14:6:20:30 (Monomer (D):Monomer (E):Monomer (E):Monomer (C):Monomer (F)), and 1,4-dioxane in 1.5 times mass based on the total amount of all monomers was added thereto. To the resultant mixture, azobisisobutyronitrile as an initiator in a ratio of 1.00 mol % based on all monomer molar amount, and azobis(2,4-dimethylvaleronitrile) as an initiator in a ratio of 3.00 mol % based on all monomer molar amount were added. The obtained mixture was heated at 73° C. for about 5 hours. Then, the reaction mixture obtained was poured into a large amount of a mixture of methanol and water (mass ratio of methanol to water (methanol/water) was 4/1) to cause precipitation. The precipitate was isolated by filtration and dissolved in 1,4-dioxane. The resultant solution was poured into a large amount of a mixture of methanol and water to cause precipitation, and this operation was repeated twice for purification. As a result, a resin having a weight-average molecular weight of about $8.1 \times 10^3$ was obtained in a yield of 65%. This is called as Resin A1. Resin A1 had the structural units derived from Monomer (U), Monomer (E), Monomer (B), Monomer (C) and Monomer (F).

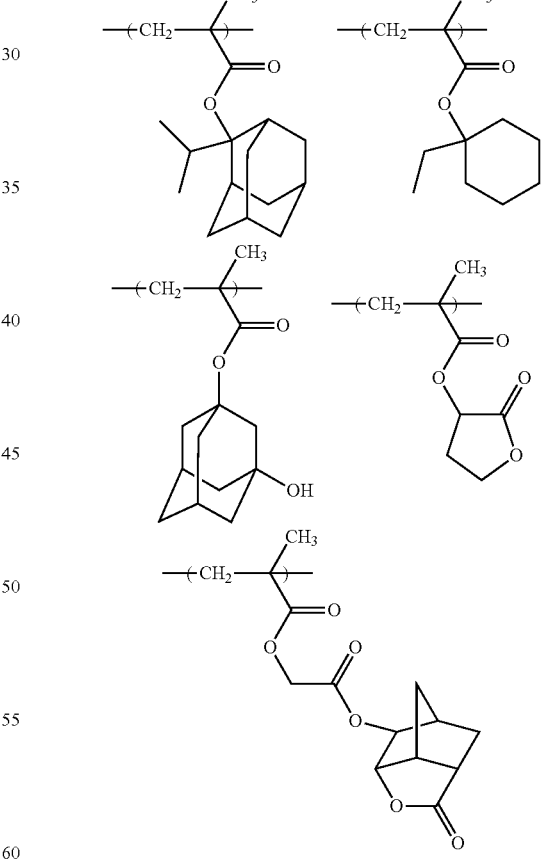

Resin Synthesis Example 2

Monomer (A), Monomer (E), Monomer (B), Monomer (C) and Monomer (F) were mixed at a molar ratio of 30:14:6:20:30 (Monomer (A):Monomer (E):Monomer (B):Monomer (C):Monomer (F)), and 1,4-dioxane in 1.5 times mass based on the total amount of all monomers was added thereto. To the resultant mixture, azobisisobutyronitrile as an initiator in a ratio of 1.00 mol % based on all monomer molar amount, and azobis(2,4-dimethylvaleronitrile) as an initiator in a ratio of 3.00 mol % based on all monomer molar amount were added. The obtained mixture was heated at 73° C. for about 5 hours. Then, the reaction mixture obtained was poured into a large amount of a mixture of methanol and water (mass ratio of methanol to water (methanol/water) was 4/1) to cause precipitation. The precipitate was isolated by filtration and dissolved in 1,4-dioxane. The resultant solution was poured into a large amount of a mixture of methanol and water to cause precipitation, and this operation was repeated three times for purification. As a result, a resin having a weight-average molecular weight of about $7.8 \times 10^3$ was obtained in a yield of 68%. This is called as Resin A2. Resin A2 had the structural units derived from Monomer (A), Monomer (E), Monomer (B), Monomer (C) and Monomer (F).

Then, the reaction mixture obtained was poured into a large amount of a mixture of methanol and water (mass ratio of methanol to water (methanol/water) was 4/1) to cause precipitation. The precipitate was isolated by filtration and dissolved in 1,4-dioxane. The resultant solution was poured into a large amount of a mixture of methanol and water to cause precipitation, and this operation was repeated three times for purification. As a result, a resin having a weight-average molecular weight of about $9.2 \times 10^3$ was obtained in a yield of 60%. This is called as Resin A3. Resin A3 had the structural units derived from Monomer (A), Monomer (B) and Monomer (C).

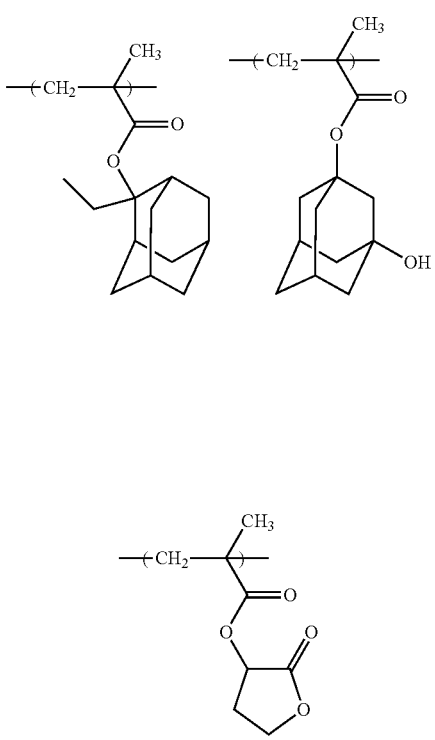

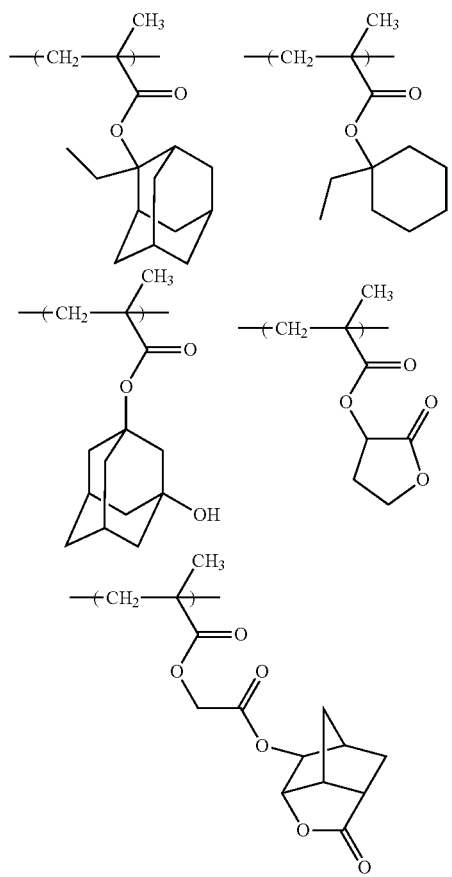

Resin Synthesis Example 4

Monomer (A), Monomer (E), Monomer (B), Monomer (F) and Monomer (C) were mixed at a molar ratio of 30:14:6:20:30 (Monomer (A):Monomer (E):Monomer (B):Monomer (F):Monomer (C)), and 1,4-dioxane in 1.5 times mass based on the total amount of all monomers was added thereto. To the resultant mixture, azobisisobutyronitrile as an initiator in a ratio of 1 mol % based on all monomer molar amount, and azobis(2,4-dimethylvaleronitrile) as an initiator in a ratio of 3 mol % based on all monomer molar amount were added. The obtained mixture was heated at 75° C. for about 5 hours. Then, the reaction mixture obtained was poured into a large amount of a mixture of methanol and water to cause precipitation. The precipitate was isolated by filtration and dissolved in 1,4-dioxane. The resultant solution was poured into a large amount of a mixture of methanol and water to cause precipitation, and this operation was repeated twice for purification. As a result, a resin having a weight-average molecular weight of about $7.2 \times 10^3$ was obtained in a yield of 78%. This is called as Resin A4. Resin A4 had the structural units derived from Monomer (A), Monomer (E), Monomer (B), Monomer (F) and Monomer (C).

Resin Synthesis Example 3

Monomer (A), Monomer (B) and Monomer (C) were mixed at a molar ratio of 50:25:25 (Monomer (A):Monomer (B):Monomer (C)), and 1,4-dioxane in 1.5 times mass based on the total amount of all monomers was added thereto. To the resultant mixture, azobisisobutyronitrile as an initiator in a ratio of 1 mol % based on all monomer molar amount, and azobis (2,4-dimethylvaleronitrile) as an initiator in a ratio of 3 mol % based on all monomer molar amount were added. The obtained mixture was heated at 80° C. for about 8 hours.

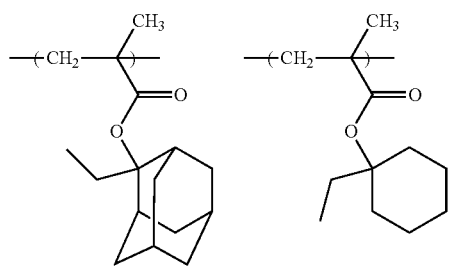

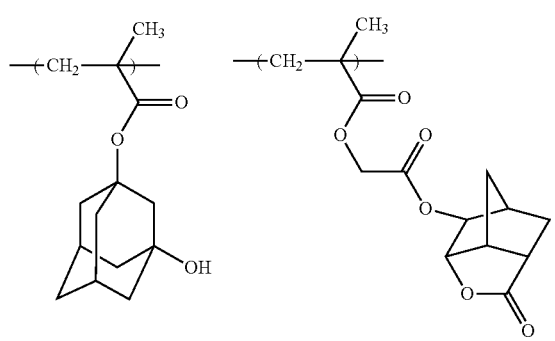

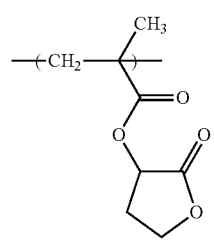

Resin Synthesis Example 5

Monomer (A), Monomer (G), Monomer (B), Monomer (F) and Monomer (C) were mixed at a molar ratio of 30:14:6:20:30 (Monomer (A):Monomer (G):Monomer (B):Monomer (F):Monomer (C)), and 1,4-dioxane in 1.5 times mass based on the total amount of all monomers was added thereto. To the resultant mixture, azobisisobutyronitrile as an initiator in a ratio of 1 mol % based on all monomer molar amount, and azobis(2,4-dimethylvaleronitrile) as an initiator in a ratio of 3 mol % based on all monomer molar amount were added. The obtained mixture was heated at 75° C. for about 5 hours. Then, the reaction mixture obtained was poured into a large amount of a mixture of methanol and water to cause precipitation. The precipitate was isolated by filtration and dissolved in 1,4-dioxane. The resultant solution was poured into a large amount of a mixture of methanol and water to cause precipitation, and this operation was repeated twice for purification. As a result, a resin having a weight-average molecular weight of about $7.2 \times 10^3$ was obtained in a yield of 78%. This is called as Resin A5. Resin A5 had the structural units derived from Monomer (A), Monomer (G), Monomer (B), Monomer (F) and Monomer (C).

Examples 8 to 34 and Comparative Example 1

<Resin>

Resin A1, A2, A3, A4, A5

<Acid Genertor>

B1: Salt represented by the following formula

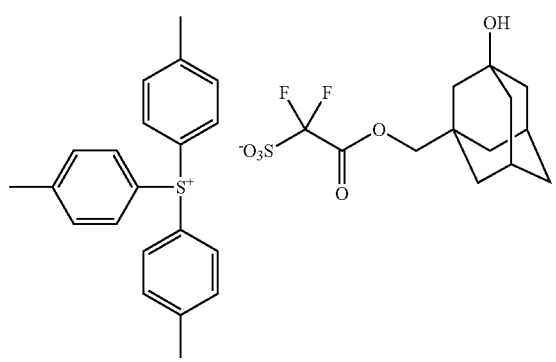

B2: Salt represented by the following formula

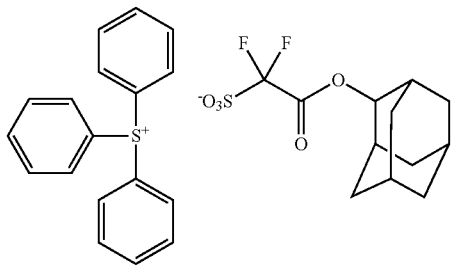

<Basic Compound>
C1: 2,6-diisopropylaniline
<Compound (I)>
I1: Compound represented by the formula (I-1)
I2: Compound represented by the formula (I-2)
I3: 3-ethyl-3-oxetanemetahnol available from Tokyo Chemical Industry Co., Ltd.

I4: Compound represented by the formula (I-4)
I5: Compound represented by the formula (I-5)
I6: Compound represented by the formula (I-6)
I7: Compound represented by the formula (I-7)
I8: 1-hydroxy-2,3-epoxypropane available from Tokyo Chemical Industry Co., Ltd.

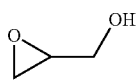

I9: Compound represented by the formula (I-9)
<Solvent>

| E1: | propylene glycol monomethyl ether acetate | 265 parts |
| | propylene glycol monomethyl ether | 20.0 parts |
| | γ-butyrolactone | 3.5 parts |
| | 2-heptanone | 20.0 parts |

The following components were mixed and dissolved, further, filtrated through a fluorine resin filter having pore diameter of 0.2 μm, to prepare photoresist compositions, Resin (kind and amount are described in Table 1)
Acid generator (kind and amount are described in Table 1)
Compound (I) (kind and amount are described in Table 1)
Basic compound (kind and amount are described in Table 1)
Solvent (kind and amount are described in Table 1)

TABLE 1

| | Resin (kind/amount (part)) | Acid Generator (kind/amount (part)) | Compound (I) (kind/amount (part)) | Basic Compound (kind/amount (part)) | Solvent |
|---|---|---|---|---|---|
| Ex. 8 | A1/10 | B1/1.00 | I1/0.3 | — | E1 |
| Ex. 9 | A2/10 | B1/1.00 | I1/0.3 | — | E1 |
| Ex. 10 | A1/10 | B1/1.00 | I1/0.2 | C1/0.07 | E1 |
| Ex. 11 | A2/10 | B1/1.00 | I1/0.2 | C1/0.07 | E1 |
| Ex. 12 | A2/10 | B1/1.00 | I2/0.3 | — | E1 |
| Ex. 13 | A2/10 | B1/1.00 | I2/0.2 | C1/0.07 | E1 |
| Ex. 14 | A2/10 | B1/1.00 | I3/0.3 | — | E1 |
| Ex. 15 | A2/10 | B1/1.00 | I3/0.2 | C1/0.07 | E1 |
| Ex. 16 | A2/10 | B1/1.00 | I4/0.3 | — | E1 |
| Ex. 17 | A2/10 | B1/1.00 | I4/0.2 | C1/0.07 | E1 |
| Ex. 18 | A2/10 | B1/1.00 | I5/0.2 | C1/0.07 | E1 |
| Ex. 19 | A3/10 | B1/1.00 | I1/0.3 | — | E1 |
| Ex. 20 | A3/10 | B1/1.00 | I1/0.2 | C1/0.07 | E1 |
| Ex. 21 | A3/10 | B2/1.00 | I1/0.2 | C1/0.07 | E1 |
| Ex. 22 | A3/10 | B2/1.00 | I1/0.2 | — | E1 |
| Ex. 23 | A4/10 | B1/1.00 | I4/0.3 | — | E1 |
| Ex. 24 | A4/10 | B1/1.00 | I4/0.2 | C1/0.07 | E1 |
| Ex. 25 | A5/10 | B1/1.00 | I4/0.3 | — | E1 |
| Ex. 26 | A5/10 | B1/1.00 | I4/0.2 | C1/0.07 | E1 |
| Ex. 27 | A5/10 | B1/1.00 | I6/0.3 | — | E1 |
| Ex. 28 | A5/10 | B1/1.00 | I6/0.2 | C1/0.07 | E1 |
| Ex. 29 | A5/10 | B1/1.00 | I7/0.3 | — | E1 |
| Ex. 30 | A5/10 | B1/1.00 | I7/0.2 | C1/0.07 | E1 |
| Ex. 31 | A5/10 | B1/1.00 | I8/0.3 | — | E1 |
| Ex. 32 | A5/10 | B1/1.00 | I8/0.2 | C1/0.07 | E1 |
| Ex. 33 | A5/10 | B1/1.00 | I9/0.3 | — | E1 |
| Ex. 34 | A5/10 | B1/1.00 | I9/0.2 | C1/0.07 | E1 |
| Comp. Ex. 1 | A3/10 | B2/1.00 | — | C1/0.07 | E1 |

TABLE 2

| | PB (° C.) | PB (° C.) |
|---|---|---|
| Ex. 8 | 100 | 95 |
| Ex. 9 | 110 | 105 |
| Ex. 10 | 100 | 95 |
| Ex. 11 | 110 | 105 |
| Ex. 12 | 110 | 105 |
| Ex. 13 | 110 | 105 |
| Ex. 14 | 110 | 105 |
| Ex. 15 | 110 | 105 |
| Ex. 16 | 110 | 105 |
| Ex. 17 | 110 | 105 |
| Ex. 18 | 110 | 105 |
| Ex. 19 | 110 | 105 |
| Ex. 20 | 110 | 105 |
| Ex. 21 | 110 | 105 |
| Ex. 22 | 110 | 105 |
| Ex. 23 | 110 | 105 |
| Ex. 24 | 110 | 105 |
| Ex. 25 | 110 | 105 |
| Ex. 26 | 110 | 105 |
| Ex. 27 | 110 | 105 |
| Ex. 28 | 110 | 105 |
| Ex. 29 | 110 | 105 |
| Ex. 30 | 110 | 105 |
| Ex. 31 | 110 | 105 |
| Ex. 32 | 110 | 105 |
| Ex. 33 | 110 | 105 |
| Ex. 34 | 110 | 105 |
| Comp. Ex. 1 | 110 | 105 |

Silicon wafers (12 inches) were each coated with "ARC-29", which is an organic anti-reflective coating composition available from Nissan Chemical Industries, Ltd., and then baked under the conditions; 205° C., 60 seconds, to form a 78 nm-thick organic anti-reflective coating. Each of the photoresist compositions prepared in Examples 8 to 34 and Comparative Example 1 was spin-coated over the anti-reflective coating so that the thickness of the resulting film became 85 nm after drying. The silicon wafers thus coated with the respective photoresist compositions were each prebaked on a direct hotplate at a temperature shown in column of "PB" of Table 2 for 60 seconds. Using an ArF excimer laser stepper for immersion exposure ("XT:1900Gi" manufactured by ASML, NA=1.15, 2-poles on axis illumination ($\sigma_{out}$=0.97, $\sigma_{in}$=0.77) Y polarization), each wafer thus formed with the respective photoresist film was subjected to exposure using photomasks having a line and space pattern, with the exposure quantity being varied stepwise. As the immersion medium, ultrapure water was used.

After the exposure, each wafer was subjected to post-exposure baking on a hotplate at a temperature shown in column of "PEB" of Table 2 for 60 seconds and then to paddle development for 60 seconds with an aqueous solution of 2.38 wt % tetramethylammonium hydroxide.

Each of line and space patterns developed on the organic anti-reflective coating substrate after the development was observed with a scanning electron microscope, the results of which are shown in Table 3.

Effective Sensitivity (ES): It was expressed as the amount of exposure that the line and space pattern of 50 nm became 1:1 after exposure through line and space pattern mask and development.

Line Edge Roughness (LER): The photoresist pattern at ES was observed with a scanning electron microscope. The difference between the height of the highest point and height of the lowest point of the scabrous wall surface of the photoresist pattern was measured. When the difference is 3.5 nm or less, LER is very good and its evaluation is marked by "⊚", when the difference is more than 3.5 nm and 5.5 nm or less, LER is good and its evaluation is marked by "○", and when the difference is more than 5.5 nm, LER is bad and its evaluation is marked by "X". Further, each of the differences is also shown in parentheses in a column of "LER". The smaller the difference is, the better the pattern is. The difference was shown in parentheses in Table 3.

TABLE 3

| | LER |
|---|---|
| Ex. 8 | ⊚ (3.28 nm) |
| Ex. 9 | ⊚ (3.02 nm) |
| Ex. 10 | ⊚ (3.21 nm) |
| Ex. 11 | ⊚ (3.06 nm) |
| Ex. 12 | ⊚ (2.97 nm) |
| Ex. 13 | ⊚ (2.98 nm) |
| Ex. 14 | ⊚ (3.47 nm) |
| Ex. 15 | ⊚ (3.36 nm) |
| Ex. 16 | ⊚ (2.78 nm) |
| Ex. 17 | ⊚ (2.76 nm) |
| Ex. 18 | ⊚ (2.75 nm) |
| Ex. 19 | ○ (3.85 nm) |
| Ex. 20 | ○ (3.92 nm) |
| Ex. 21 | ○ (4.92 nm) |
| Ex. 22 | ○ (5.38 nm) |
| Ex. 23 | ⊚ (2.75 nm) |
| Ex. 24 | ⊚ (2.73 nm) |
| Ex. 25 | ⊚ (2.73 nm) |
| Ex. 26 | ⊚ (2.74 nm) |
| Ex. 27 | ⊚ (2.72 nm) |
| Ex. 28 | ⊚ (2.72 nm) |
| Ex. 29 | ⊚ (2.96 nm) |
| Ex. 30 | ⊚ (2.82 nm) |
| Ex. 31 | ○ (3.88 nm) |
| Ex. 32 | ○ (3.62 nm) |
| Ex. 33 | ⊚ (2.89 nm) |
| Ex. 34 | ⊚ (2.84 nm) |
| Comp. Ex. 1 | X (6.24 nm) |

The photoresist composition of the present invention provides a good resist pattern having good line edge roughness, and is suitable for ArF excimer laser lithography, EUV lithography and EB lithography, especially suitable for immersion lithography.

What is claimed is:

1. A photoresist composition comprising
a resin which comprises a structural unit derived from a compound having an acid-labile group and which is insoluble or poorly soluble in an alkali aqueous solution but becomes soluble in an alkali aqueous solution by the action of an acid,
an acid generator and
a compound represented by the formula (I):

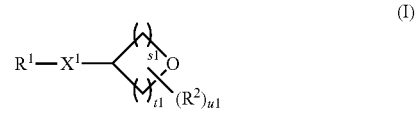

wherein $R^1$ represents a hydroxyl group, a C1-C8 alkyl group, a C3-C12 alicyclic hydrocarbon group or a C6-C18 aromatic hydrocarbon group, and one or more hydrogen atom in the alicyclic hydrocarbon group and the aromatic hydrocarbon group may be substituted with a hydroxyl group or a C1-C6 alkyl group, and one or more —$CH_2$— in the alicyclic hydrocarbon group may be replaced by —O—, —CO—, —S— or —$SO_2$—,
$X^1$ represents a C1-C12 divalent saturated hydrocarbon group in which one or more —$CH_2$— are replaced by —CO— and may be replaced by —O—,
$R^2$ is independently in each occurrence a C1-C12 saturated hydrocarbon group,
u1 represents an integer of 0 to 2, s1 represents 1 or 2, t1 represents 0 or 1 with the proviso that sum of s1 and t1 is 1 or 2.

2. The photoresist composition according to claim 1, wherein the content of the compound represented by the formula (I) is 0.01 to 5% by mass based on the solid content of the photoresist composition.

3. The photoresist composition according to claim 1, wherein $X^1$ is *—CO—O—$CH_2$—, *—$CH_2$—O—CO—O—$CH_2$—, *—O—$CH_2$—CO—O—$CH_2$—, or *—O—CO—O—$CH_2$— in which * represents a binding position to $R^1$.

4. The photoresist composition according to claim 1, wherein $X^1$ is *—CO—O—$CH_2$— in which * represents a binding position to $R^1$.

5. The photoresist composition according to claim 1, wherein $R^1$ is a C6-C12 alicyclic hydrocarbon group or a C6-C12 aromatic hydrocarbon group, and one or more hydrogen atom in the alicyclic hydrocarbon group and the aromatic hydrocarbon group may be substituted with a hydroxyl group or a C1-C6 alkyl group, and one or more —$CH_2$— in the alicyclic hydrocarbon group may be replaced by —O— or —$SO_2$—.

6. The photoresist composition according to claim 1, wherein $R^1$ is a C6-C12 alicyclic hydrocarbon group in which one or more hydrogen atom may be substituted with a hydroxyl group or a C1-C6 alkyl group, and in which one or more —$CH_2$— may be replaced by —O— or —$SO_2$—.

7. The photoresist composition according to claim 1, wherein $R^2$ is independently in each occurrence a C1-C12 alkyl group.

8. A process for producing a photoresist pattern comprising the following steps (1) to (5):
- (1) a step of applying the photoresist composition according to any one of claims 1 to 7 on a substrate,
- (2) a step of forming a photoresist film by conducting drying,
- (3) a step of exposing the photoresist film to radiation,
- (4) a step of baking the exposed photoresist film, and
- (5) a step of developing the baked photoresist film with an alkaline developer, thereby forming a photoresist pattern.

* * * * *